(12) United States Patent
Yoshida et al.

(10) Patent No.: US 9,585,746 B2
(45) Date of Patent: Mar. 7, 2017

(54) ARTIFICIAL VALVED CONDUITS FOR CARDIAC RECONSTRUCTIVE PROCEDURES AND METHODS FOR THEIR PRODUCTION

(75) Inventors: Masahiro Yoshida, Pittsburgh, PA (US); C. Douglas Bernstein, Pittsburgh, PA (US); Onur Dur, San Ramon, CA (US); Kerem Pekkan, Pittsburgh, PA (US)

(73) Assignees: Carnegie Mellon University, Pittsburgh, PA (US); University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 131 days.

(21) Appl. No.: 14/235,578

(22) PCT Filed: Jul. 30, 2012

(86) PCT No.: PCT/US2012/048902
§ 371 (c)(1),
(2), (4) Date: Apr. 1, 2014

(87) PCT Pub. No.: WO2013/019756
PCT Pub. Date: Feb. 7, 2013

(65) Prior Publication Data
US 2014/0288642 A1 Sep. 25, 2014

Related U.S. Application Data

(60) Provisional application No. 61/574,254, filed on Jul. 29, 2011, provisional application No. 61/628,209, (Continued)

(51) Int. Cl.
*A61F 2/24* (2006.01)
*A61L 27/16* (2006.01)
(Continued)

(52) U.S. Cl.
CPC .......... *A61F 2/2409* (2013.01); *A61F 2/2403* (2013.01); *A61F 2/2415* (2013.01);
(Continued)

(58) Field of Classification Search
CPC ........ A61F 2/24; A61F 2/2409; A61F 2/2412; A61F 2/06; A61F 2/2403; A61F 2/2415;
(Continued)

(56) References Cited

U.S. PATENT DOCUMENTS 4,187,390 A 2/1980 Gore
4,955,899 A 9/1990 Della Corna et al.
(Continued)

OTHER PUBLICATIONS

Ando et al., Ten-year experience with handmade trileaflet polytetrafluoroethylene valved conduit used for pulmonary reconstruction, *J Thorac Cadiovasc Surg*, (2009), 137:124-131.
(Continued)

*Primary Examiner* — Thomas J Sweet
*Assistant Examiner* — Seema Mathew
(74) *Attorney, Agent, or Firm* — Pepper Hamilton LLP

(57) ABSTRACT

Artificial heart valve structures and methods of their fabrication are disclosed. The heart valve structures may be fabricated from a biocompatible polymer and include one or more heart valve leaflet structures incorporated within a conduit. The valve structures may incorporate one or more conduit sinuses, as well as a gap between the lower margin of the valve leaflets and the interior of the conduit. In addition, the valve structures may include one or more valve sinuses created in a space between the valve leaflets and the conduit inner surface. Computational fluid dynamics and mechanical modeling may be used to design the valve leaflets with optimal characteristics. A heart valve structure may also incorporate a biodegradable component to which cells may adhere The incorporated cells may arise from
(Continued)

patient cells migrating to the biodegradable component, or the component may be pre-seeded with cells prior to implantation in a patient.

13 Claims, 11 Drawing Sheets

Related U.S. Application Data filed on Oct. 26, 2011, provisional application No. 61/633,634, filed on Feb. 14, 2012.

(51) Int. Cl.
    *A61L 33/00*     (2006.01)
    *A61F 2/06*     (2013.01)

(52) U.S. Cl.
    CPC ............ *A61L 27/16* (2013.01); *A61L 33/0011* (2013.01); *A61F 2/06* (2013.01); *A61F 2/2412* (2013.01); *A61F 2/2475* (2013.01); *A61F 2250/0082* (2013.01); *A61L 2430/20* (2013.01); *Y10T 29/49412* (2015.01)

(58) Field of Classification Search
    CPC ............ A61F 2250/0082; A61F 2/2475; A61F 2/249; A61L 27/16; A61L 2430/20; A61L 33/0011; Y10S 623/90
    See application file for complete search history.

(56) References Cited

U.S. PATENT DOCUMENTS

| | | | |
|---|---|---|---|
| 5,800,512 A | 9/1998 | Lentz et al. | |
| 5,804,011 A | 9/1998 | Dutta et al. | |
| 6,016,848 A | 1/2000 | Egres, Jr. | |
| 6,436,135 B1 | 8/2002 | Goldfarb | |
| 6,517,571 B1 | 2/2003 | Brauker et al. | |
| 6,716,239 B2 | 4/2004 | Sowinski et al. | |
| 6,863,686 B2 | 3/2005 | Shannon et al. | |
| 6,939,372 B2 | 9/2005 | Dong | |
| 7,306,729 B2 | 12/2007 | Bacino et al. | |
| 7,789,908 B2 | 9/2010 | Sowinski et al. | |
| 8,672,997 B2* | 3/2014 | Drasler | A61F 2/2418 623/1.24 |
| 2002/0055775 A1* | 5/2002 | Carpentier | A61F 2/2412 623/2.17 |
| 2002/0138135 A1 | 9/2002 | Duerig et al. | |
| 2003/0027332 A1* | 2/2003 | Lafrance | A61F 2/2412 435/366 |
| 2003/0114924 A1* | 6/2003 | Moe | A61F 2/2412 623/2.12 |
| 2003/0139805 A1 | 7/2003 | Holmberg et al. | |
| 2003/0191525 A1* | 10/2003 | Thornton | A61F 2/2475 623/1.24 |
| 2005/0075727 A1* | 4/2005 | Wheatley | A61F 2/2457 623/2.17 |
| 2005/0137682 A1 | 6/2005 | Justino | |
| 2005/0228495 A1* | 10/2005 | Macoviak | A61F 2/2412 623/2.18 |
| 2006/0149366 A1 | 7/2006 | Henderson | |
| 2006/0161248 A1 | 7/2006 | Case et al. | |
| 2006/0229716 A1* | 10/2006 | Mitrev | A61B 5/1072 623/2.11 |
| 2006/0259136 A1 | 11/2006 | Nguyen et al. | |
| 2006/0265053 A1* | 11/2006 | Hunt | A61F 2/2412 623/1.24 |
| 2007/0027528 A1* | 2/2007 | Agnew | A61F 2/2412 623/1.24 |
| 2007/0043431 A1* | 2/2007 | Melsheimer | 623/1.24 |
| 2009/0118826 A1 | 5/2009 | Khaghani | |
| 2011/0094592 A1* | 4/2011 | Cheng | A61F 2/2403 137/1 |
| 2011/0166637 A1 | 7/2011 | Irwin et al. | |
| 2013/0013058 A1* | 1/2013 | Umezu | A61F 2/2412 623/2.12 |
| 2013/0166016 A1 | 6/2013 | Cully et al. | |
| 2013/0184807 A1 | 7/2013 | Kovach et al. | |
| 2014/0155995 A1* | 6/2014 | Sun | A61F 2/2412 623/2.18 |
| 2016/0015516 A1* | 1/2016 | Bernstein | A61F 2/24 623/1.15 |
| 2016/0067038 A1* | 3/2016 | Park | A61F 2/2406 623/2.18 |

OTHER PUBLICATIONS

Bativala et al., Pulmonary Valve Replacement Function in Adolescents: A Comparison of Bioprosthetic Valves and Homograft Conduits, *Ann Thorac Surg*, (2012), 93:2007-2016.
Bernstein et al., Bicuspid-Valved PTFE Conduit Optimization for Pediatric RVOT Reconstruction, Bioengineering Conference (NEBEC), (2011).
Bianca et al., Sex ratio imbalance in transposition of the great arteries and possible agricultural environmental risk factors, *Images Paediatr Cardiol*, (2001), 8:10-14.
Bielefeld et al., Reoperative Homograft Right Ventricular Outflow Tract Reconstruction, *Ann Thorac Surg*, (2001), 71(2):482-488.
Boethig et al., Mid term course after pediatric right ventricular outflow tract reconstruction: a comparison of homografts, porcine xenografts and Contegras, *European Journal of Cardio-thoracic Surgery*, (2005), 27:58-66.
Boudjemline et al., Use of bovine jugular vein to reconstruct the right ventricular outflow tract: Early results, *J Thome Cardiovasc Surg*, (2003), 126:490-497.
Brown et al., Right ventricular outflow tract reconstruction with polytetrafluoroethylene monocusp valve: A twelve-year experience, *J Thorac Cardiovasc Surg*, (2007), 133(5):13361343.
Caldarone et al., Independent Factors Associated with Longevity of Prosthetic Pulmonary Valves and Valved Conduits, *J Thorac Cardiovasc Surg*, (2000), 120:1022-1031.
Canfield et al., National Estimates and Race/Ethnic-Specific Variation of Selected Birth Defects in the United States, *Birth Defects Research (Part A): Clinical and Molecular Teratology*, (2006), 76:747-756.
Chrysosotomou et al., Chapter 21: Tetralogy of Fallot with Pulmonary Atresia, *Critical Care of Children with Heart Disease: Basic Medical and Surgical Concepts*, (2010), 213-219.
Chrysosotomou et al., Chapter 22: Pulmonary Atresia with Intact Interventricular Septum, *Critical Care of Children with Heart Disease: Basic Medical and Surgical Concepts*, (2010), 221-229.
Cruz et al., Truncus Arteriosus, Chapter 35, Critical Care of Children with Heart Disease, Springer, (2009).
DeFrances et al., National Hospital Discharge Survey: 2005 annual summary with detailed diagnosis and procedure data, *National Center for Health Statistics, Vital Health Stat* (2007), 13(165):1-218.
Dur et al., in Vitro Evaluation of Right Ventricular Outflow Tract Reconstruction With Bicuspid Valved Polytetrafluoroethylene Conduit, *Artificial Organs*, (2010), 34: 1010-1016.
Erek et al., Durability of Stentless Bioprostheses for Right Ventricular Outflow Tract Reconstruction, *Ann Thorac Surg*, (2005), 79(6): 2202-2203.
Forbess et al., Cryopreserved Homografts in the Pulmonary Position: Determinants of Durability, *Ann Thorac Surg*, (2001), 71(1):54-59.
Forbess et al., Conduit selection for right ventricular outflow tract reconstruction: contemporary options and outcomes, *Semin Thorac Cardiovasc Surg Pediatr Card Surg Annu*, (2004), 7:115-124.
Fung, Biodynamics-circulation, Springer-verlag, New York-Berlin-Heidelberg-Tokyo 1984, 404 p. 189.
Gober et al., Adverse Mid-Term Outcome Following RVOT Reconstruction Using the Contegra Valved Bovine Jugular Vein, *Ann Thorac Surg*, (2005), 79:625-631.

(56) References Cited

OTHER PUBLICATIONS

Graham et al, Comparison of Norwood Shunt Types: Do the Outcomes Differ 6 Years Later?, *Ann Thorac Surg*, (2010), 90:31-35.
Hamilton et al., Births: Preliminary Data for 2009, *National Vital Statistics Reports*, (Dec. 21, 2010), 59(3):1-19.
Heron et al., Deaths: Final Data for 2006, National Vital Statistics Reports, (Apr. 17, 2009), 57(14):1-135.
Hoffman, Chapter 21: Congenital Heart Disease, *Essential Cardiology: Principles and Practice*, 2nd Ed., 393-406.
Hoffman, The Incidence of Congenital Heart Disease, *J. Am. Coll. Cardiol.*, (2002), 39(12):1890-1900.
Hoyert et al., Annual Summary of Vital Statistics: 2004, *Pediatrics*, (2006):168-183.
Kaza et al., Long-term results of right ventricular outflow tract reconstruction in neonatal cardiac surgery: Options and outcomes, *J Thorac Cardiovasc Surg*, (2009), 138:911-916.
Menon et al., Regional Myocardial Dysfunction following Norwood with Right Ventricle to Pulmonary Artery Conduit in Patients with Hypoplastic Left Heart Syndrome, *Journal of the American Society of Echocardiography*, (2011), 24(8):827-833.
Meyns et al., The Contegra conduit in the right ventricular outflow tract induces supravalvular stenosis, *J Thorac Cardiovasc Surg*, (2004), 128:834-840.
Miyazaki et al., Expanded polytetrafluoroethylene conduits and patches with bulging sinuses and fan-shaped valves in right ventricular outflow tract reconstruction: Multicenter study in Japan, *J Thorac Cardiovasc Surg*, (2011), 142:1122-1129.
Naheed et al., Chapter 16 Pulmonary Atresia with Intact Ventricular Septum, *Heart Diseases in Children: A Pediatrician's Guide*, (2011), 195-202.
Niwa et al., Progressive Aortic Root Dilation in Adults and Late After Repair of Tetralogy of Fallot, *Circulation*, (2002), 106:1374-1378.
Ohye, Comparison of Right Ventricle to Pulmonary Artery Conduit and Modified Blalock-Taussig Shunt Hemodynamics After the Norwood Operation, Ann Thorac Surg, (2004), 78:1090-1093.
Oury, The Ross Procedure: Currently Registry Results, *Ann Thorac Surg*, (1998), 66:S162-S165.
Parker et al., Updated National Birth Prevalence Estimates for Selected Birth Defects in the United States, 2004-2006, *Birth Defects Research (Part A): Clinical and Molecular Tetratology*, (2010), 88:1008-1016.
Proptopapas et al., Contegra conduit for reconstruction of the right ventricular outflow tract: a review of published early and mid-time results, *Journal of Cardiothoracic Surgery*, (2008), 3:62 (7 pages).
Rosti et al., Mechanical valves in the pulmonary position: a reappraisal, *J Thorac Cardiovasc Surg*, (1998), 115(5):1074-1079.
Sano et al., Right ventricle-pulmonary artery shunt in first-stage palliation of hypoplastic left heart syndrome, J Thorac Cardiovasc Surg, (2003), 126:504-510.
Schreiber et al., Early Graft Failure of Small-Sized Porcine-Valved Conduits in Reconstruction of Right Ventricular Outflow Tract, *Ann Thorac Surg*, (2006), 82:179-186.
Shebani et al., Right ventricular outflow tract reconstruction using Contegra valved conduit: natural history and conduit performance under pressure, *European Journal of Cardio-thoracic Surgery*, (2006), 29:397-405.
Shiose et al., Recent Advances and Patents on Circulatory Support Devices for Pediatric Patients, *Recent Patents on Biomedical Engineering*, (2009), 2:161-164.
Stefano et al., Right ventricle outflow tract reconstruction in the pediatric population: A comparative analysis between different grafts, The 15th Congress on Cardio-Thoracic Surgery, (Nov. 2010).
Wang et al., In vivo degradation characteristics of poly(glycerol sebacate), J Biomed Mater Res A, (2003), 66A:192-197.
Wald et al., Refining the assessment of pulmonary regurgitation in adults after tetralogy of Fallot repair: should we be measuring regurgitant fraction or regurgitant volume?, *European Heart Journal*, (2009), 30:356-361.
Yoganathan et al., Fluid mechanics of heart valves, Annu Rev Biomed Eng, (2004), 6:331-362.
Yoshida et al., Right Ventricular Outflow Tract Reconstruction with Bicuspid Valved Polytetrafluoroethylene Conduit, *Annals of Thoracic Surgery*, (2011), 91:1235-1239.
Yoshida et al., Midterm results of bicuspid valved PTFE conduit for right ventricular outflow tract reconstruction, *The 48th Annual Meeting of STS* (2012) Abstract.
Yuan et al., Right ventricular outflow tract reconstruction: valve conduit of choice and clinical outcomes, J Cardiovasc Med, (2008), 9(4):327-337.
PCT/US2012/048902 International Search Report dated Oct. 5, 2012.

* cited by examiner

ARTIFICIAL VALVED CONDUITS FOR CARDIAC RECONSTRUCTIVE PROCEDURES AND METHODS FOR THEIR PRODUCTION

CLAIM OF PRIORITY

The present application is a U.S. national stage filing under 35 U.S.C. §371 of International Application No. US2012/048902 filed Jul. 30, 2012 entitled "Artificial Valved Conduits for Cardiac Reconstructive Procedures and Methods for Their Production," which in turn claims the benefit of and priority to U.S. Provisional Application No. 61/574,254 filed on Jul. 29, 2011, entitled "A Patient-Specific, Bicuspid-Valved Conduit for Pediatric Right Ventricular Outflow Tract Reconstruction," U.S. Provisional Application No. 61/628,209 filed on Oct. 26, 2011 entitled "A Hybrid Tissue-Engineered Valved Conduit (Hybrid TEVC) for the Reconstruction of the Pediatric Right Ventricular Outflow Tract (RVOT)", and U.S. Provisional Application No. 61/633,634 filed on Feb. 14, 2012 entitled "A Valve Shunt for the Treatment of Hypoplastic Left Heart Syndrome," the disclosures of which are incorporated by reference in their entireties.

BACKGROUND

The selection of a heart valve structure for right ventricle outflow tract (RVOT) reconstruction may present a major challenge in the treatment of many congenital heart diseases including, without limitation, tetralogy of Fallot with pulmonary atresia, truncus arteriosus, transposition of great arteries with pulmonary stenosis, and congenital aortic stenosis/insufficiency.

Heart valve structures that may be used for RVOT reconstruction in pediatric patients may consist of homografts, which may not be readily available in many cases, and xenografts, which may be expensive (frequently around $4,000-$5,000). After the invention of the cryopreservation process in early 1980s, and especially with the increased availability of a wide range of sizes, the homograft has frequently become the heart surgeon's heart valve structure of choice for the RVOT reconstruction. However, longitudinal studies have demonstrated that homografts may also necessitate heart valve structure replacement due to stenosis and insufficiency. Such complications may be caused by shrinkage and calcification, and may be especially problematic for younger patients.

Recently, new xenograft designs have been evaluated for RVOT reconstruction including a glutaraldehyde-fixed porcine aortic valve and root, and a glutaraldehyde-fixed segment of a bovine jugular vein with venous valve. Although the anatomical shape of the porcine prosthesis may fit well to the RVOT, stenosis and calcification issues may still persist when the prosthesis is implanted in children. Similarly, recent reports on the bovine heart valve structures suggest a significant early fibrotic ring formation at the distal anastomosis. Additionally, dramatic dilation of and regurgitation through a heart valve structure may occur in the setting of pulmonary hypertension or distal anastomotic ring. The most successful heart valve structures for RVOT reconstruction, the homograft and the bovine jugular vein, both have shown re-operation rates of around 10-20% after about only two years. Re-operation and re-intervention rates, especially for the bovine xenograft, appear to increase significantly with increasing time and decreasing conduit diameter.

Both homografts and xenografts may suffer from calcification, which may result in stenosis and insufficiency, leading to the need for re-operation and replacement of the heart valve structure. Additionally, studies suggest that bioprosthetic heart valve structures available for RVOT reconstruction i.e. both allografts and xenografts, may be ineffective due to poor hemodynamic performance and long-term complications, especially in very young patients. Even after bioprosthetic valve replacement is performed, frequent surgeries for RVOT reconstruction may be required until the individual reaches adulthood. The additional surgeries may be required due to recurrent stenosis/insufficiency caused by calcification or degenerative processes, as well as the relative stenosis due to somatic growth.

Artificial heart valve structures may be considered as an alternative to both homografts and xenografts. However, artificial mechanical valves may not generally be available for RVOT reconstruction for pediatric patients. One factor that may affect availability of such heart valve structures may include the difficulty of designing a valve structure which can deal with the very low pressures (which may be less than 20 mmHg in many cases) found in the pediatric RVOT. Additional design challenges may also include small conduit diameter, a high degree of curvature along the conduit path, and the need for conduit flexibility as the patient grows. Intensive bioengineering studies may be required to produce effective designs customized for the pediatric/neonatal population. In use, mechanical valves may have higher longevity when implanted in the pulmonary position compared to implantation in the aortic position, but may require aggressive anticoagulant therapy due to a higher risk of thrombosis.

In addition to those conditions disclosed above for which RVOT is indicated, other disorders may also benefit from implanted artificial heart valve structures. Hypoplastic Left Heart Syndrome (HLHS) is a rare and complex congenital heart disorder which may be extremely difficult to treat successfully. HLHS may be characterized by a hypoplastic left ventricle that is unable to maintain systemic circulation, a hypoplastic aortic arch and ascending aorta that require reconstruction, and a patent ductus arteriosus that may maintain systemic circulation of the lower body. In order to treat HLHS, three separate procedures may be required: a Norwood operation, a bidirectional Glenn procedure, and a Fontan procedure.

The Norwood operation typically involves connecting the base of the pulmonary artery to the aortic arch in order to re-direct blood flow to the systemic tract. In order to continue to provide circulation to the pulmonary tract, a shunt or conduit may be placed following the Norwood operation to provide blood flow to the pulmonary artery. At present, there are two typical options for such a shunt: a Blalock-Taussig (BT) shunt that may connect the aorta to the base of the pulmonary artery, and a Sano shunt (RV-PA conduit) that may be placed between the right ventricle and the pulmonary artery.

The placement of the BT shunt may result in blood flow from the aorta to the pulmonary artery during both systolic and diastolic phases. This constant flow due to the BT shunt may cause low systemic diastolic pressure that can potentially lead to early mortality. The RV-PA conduit may avoid the issue of the pulmonary tract constantly leaching blood flow from the systemic tract by connecting the pulmonary artery directly to the right ventricle, rather than the aorta. In this manner the RV-PA shunt can maintain higher systemic diastolic pressure than the BT shunt. However present RV-PA shunts contain no valves, so backflow may occur into the right ventricle. As a result of the backflow, right ventricular enlargement may occur leading eventually to the need for partial or total heart replacement.

Shunts used for the treatment of HLHS can be very small, normally having a diameter of around 4 mm. This can make extremely difficult the design and manufacturing of any heart valve structure containing such a conduit. Past attempts at using a simple valved conduit have been unsuccessful, as the placement and geometry of the valve have resulted in the valve sticking to the conduit. Valve sticking may result in thrombus formation and flow impedance, which often results in early patient mortality.

Therefore, there appears to be a significant need for a heart valve structure, encompassing a conduit and a heart valve leaflet structure, with long durability for use with neonatal and pediatric patients.

SUMMARY

Before the present methods are described, it is to be understood that this invention is not limited to the particular systems, methodologies or protocols described, as these may vary. It is also to be understood that the terminology used herein is for the purpose of describing particular embodiments only, and is not intended to limit the scope of the present disclosure which will be limited only by the appended claims.

For the purpose of this disclosure, the term "heart valve leaflet structure" may be defined as a valved structure for use in coronary or vascular procedures, which may be composed of one or more heart valve leaflets. The term may encompass, as non-limiting examples, a heart valve single leaflet structure having a single heart valve leaflet, or a heart valve multi-leaflet structure having more than one heart valve leaflet. Each heart valve leaflet may include a sinus edge, a fan edge, a sinus structure, and a fan structure.

For the purpose of this disclosure, the term "heart valve structure" may be defined as a valved structure for use in coronary or vascular procedures composed of one or more heart valve leaflet structures and additional structural components. Additional structural components may include, without limitation, a conduit and one or more conduit sinus structures. The term may encompass a single leaflet heart valve structure having a heart valve single leaflet structure, or a multi-leaflet heart valve structure composed of either multiple heart valve single leaflet structures or a heart valve multi-leaflet structure.

In an embodiment, a heart valve multi-leaflet structure may include a first heart valve leaflet, having a first sinus edge and a first fan edge, and a second heart valve leaflet, having a second sinus edge and a second fan edge, in which the first fan edge may intersect the second fan edge at an outer commissure point, and the first sinus edge may intersect the second sinus edge at an inner commissure point, thereby forming a commissure extending from the outer commissure point to the inner commissure point. Additionally, the first fan edge may intersect the first sinus edge at a first outer leaflet point, thereby forming a first baseline extending from the first outer leaflet point to the commissure, the first baseline further having a first width as measured from the first outer leaflet point to the commissure. Further, the second fan edge may intersect the second sinus edge at a second outer leaflet point, thereby forming a second baseline extending from the second outer leaflet point to the commissure, the second baseline further having a second width as measured from the second outer leaflet point to the commissure. In addition, the second baseline may be essentially collinear with the first baseline. The first sinus edge may also extend from and may not be coextensive with the first baseline, thereby forming a first sinus structure bounded by the first sinus edge, the commissure, and the first baseline, and the second sinus edge may extend from and may not be coextensive with the second baseline, thereby forming a second sinus structure bounded by the second sinus edge, the commissure, and the second baseline. Further, the first fan edge may extend from and may not be coextensive with the first baseline, thereby forming a first fan structure bounded by the first fan edge, the commissure, and the first baseline, and the second fan edge may extend from and may not be coextensive with the second baseline, thereby forming a second fan structure bounded by the second fan edge, the commissure, and the second baseline. In addition, the first heart valve leaflet may include a biocompatible and hemocompatible polymer, and the second heart valve leaflet may also include an effectively same the biocompatible and hemocompatible polymer.

In an embodiment, a heart valve structure may include a conduit comprising an inner conduit surface, an outer conduit surface, and a diameter, and a heart valve multi-leaflet structure. The heart valve multi-leaflet structure may include a first heart valve leaflet, having a first sinus edge and a first fan edge, and a second heart valve leaflet, having a second sinus edge and a second fan edge, in which the first fan edge may intersect the second fan edge at an outer commissure point, and the first sinus edge may intersect the second sinus edge at an inner commissure point, thereby forming a commissure extending from the outer commissure point to the inner commissure point. Additionally, the first fan edge may intersect the first sinus edge at a first outer leaflet point, thereby forming a first baseline extending from the first outer leaflet point to the commissure, the first baseline further having a first width as measured from the first outer leaflet point to the commissure. Further, the second fan edge may intersect the second sinus edge at a second outer leaflet point, thereby forming a second baseline extending from the second outer leaflet point to the commissure, the second baseline further having a second width as measured from the second outer leaflet point to the commissure. In addition, the second baseline may be essentially collinear with the first baseline. The first sinus edge may also extend from and may not be coextensive with the first baseline, thereby forming a first sinus structure bounded by the first sinus edge, the commissure, and the first baseline, and the second sinus edge may extend from and may not be coextensive with the second baseline, thereby forming a second sinus structure bounded by the second sinus edge, the commissure, and the second baseline. Further, the first fan edge may extend from and may not be coextensive with the first baseline, thereby forming a first fan structure bounded by the first fan edge, the commissure, and the first baseline, and the second fan edge may extend from and may not be coextensive with the second baseline, thereby forming a second fan structure bounded by the second fan edge, the commissure, and the second baseline. Additionally, at least a portion of the first fan edge, at least a portion of the second fan edge, and at least a portion of the inner conduit surface may be mutually disposed to form a valve gap. Further, at least a portion of the first sinus structure and a portion of the inner conduit surface may be nonadjacent, thereby forming a first valve sinus bounded at least in part by at least a portion of the inner conduit surface and at least a portion of the first sinus structure, and at least a portion of the second sinus structure and a portion of the inner conduit surface may be nonadjacent, thereby forming a second valve sinus bounded at least in part by at least a portion of the inner conduit surface and at least a portion of the second sinus structure.

In an embodiment, a method of fabricating a heart valve structure, may include providing a flexible conduit comprising a wall, an inner surface, and an outer surface; providing a heart valve multi-leaflet structure; everting the flexible conduit; affixing the heart valve multi-leaflet structure to the inner surface; and reverting the conduit, thereby forming a multi-leaflet valve within an interior of the conduit. a heart valve structure may include a conduit comprising an inner conduit surface, an outer conduit surface, and a diameter, and a heart valve multi-leaflet structure. The heart valve multi-leaflet structure may include a first heart valve leaflet, having a first sinus edge and a first fan edge, and a second heart valve leaflet, having a second sinus edge and a second fan edge, in which the first fan edge may intersect the second fan edge at an outer commissure point, and the first sinus edge may intersect the second sinus edge at an inner commissure point, thereby forming a commissure extending from the outer commissure point to the inner commissure point. Additionally, the first fan edge may intersect the first sinus edge at a first outer leaflet point, thereby forming a first baseline extending from the first outer leaflet point to the commissure, the first baseline further having a first width as measured from the first outer leaflet point to the commissure. Further, the second fan edge may intersect the second sinus edge at a second outer leaflet point, thereby forming a second baseline extending from the second outer leaflet point to the commissure, the second baseline further having a second width as measured from the second outer leaflet point to the commissure. In addition, the second baseline may be essentially collinear with the first baseline. The first sinus edge may also extend from and may not be coextensive with the first baseline, thereby forming a first sinus structure bounded by the first sinus edge, the commissure, and the first baseline, and the second sinus edge may extend from and may not be coextensive with the second baseline, thereby forming a second sinus structure bounded by the second sinus edge, the commissure, and the second baseline. Further, the first fan edge may extend from and may not be coextensive with the first baseline, thereby forming a first fan structure bounded by the first fan edge, the commissure, and the first baseline, and the second fan edge may extend from and may not be coextensive with the second baseline, thereby forming a second fan structure bounded by the second fan edge, the commissure, and the second baseline. Additionally, at least a portion of the first fan edge, at least a portion of the second fan edge, and at least a portion of the inner conduit surface may be mutually disposed to form a valve gap. Further, at least a portion of the first sinus structure and a portion of the inner conduit surface may be nonadjacent, thereby forming a first valve sinus bounded at least in part by at least a portion of the inner conduit surface and at least a portion of the first sinus structure, and at least a portion of the second sinus structure and a portion of the inner conduit surface may be nonadjacent, thereby forming a second valve sinus bounded at least in part by at least a portion of the inner conduit surface and at least a portion of the second sinus structure.

In an embodiment, a method of fabricating a heart valve leaflet structure includes providing a set of leaflet modeling parameters to a leaflet modeling computing program, calculating a heart valve leaflet structure initial model having one or more sinus edges, one or more sinus structures, one or more sinus baselines, one or more fan edges, one or more fan structures, and one or more fan baselines, mapping the one or more sinus edges of the heart valve leaflet structure initial model onto the inner surface of a conduit model, dividing the one or more sinus structures into one or more sinus structure beams, calculating the general shape of each of the one or more sinus structure beams, sectioning each sinus structure beam into one or more sinus structure beam point-elements in which at least a portion of the sinus structure beam point-elements correspond to points along the one or more sinus structure baselines, mapping the one or more fan structure baselines of the heart valve leaflet structure initial model onto the sinus structure beam point-elements correspond to points along the one or more sinus structure baselines, dividing the one or more fan structures into one or more fan structure beams, calculating the general shape of each of the one or more fan structure beams, sectioning each fan structure beam into one or more fan structure beam point-elements, creating a point-element aggregate from the fan structure beam point elements and the sinus structure beam point-elements, calculating a point-element aggregate mesh representation, smoothing the point element aggregate mesh representation, calculating a solid structure model from the smoothed point-element aggregate mesh representation thereby forming a heart valve leaflet model, providing fluid flow parameters and the solid structure model to a fluid flow analysis, calculating a valve performance cost function, repeating the solid modeling and fluid flow analyses until the valve performance cost function is minimal, and providing a set of heart valve leaflet size parameters corresponding to the solid model having the minimal valve performance cost function value.

In an embodiment, a hybrid tissue-engineered valved conduit includes a conduit having an inner conduit surface, an outer conduit surface, a diameter, and at least one conduit breach having a first conduit breach edge and a second conduit breach edge, a heart valve multi-leaflet structure, and at least one biodegradable structure having a first side affixed to the first conduit breach edge and a second side affixed to the second conduit breach edge. The heart valve multi-leaflet structure may include a first heart valve leaflet, having a first sinus edge and a first fan edge, and a second heart valve leaflet, having a second sinus edge and a second fan edge, in which the first fan edge may intersect the second fan edge at an outer commissure point, and the first sinus edge may intersect the second sinus edge at an inner commissure point, thereby forming a commissure extending from the outer commissure point to the inner commissure point. Additionally, the first fan edge may intersect the first sinus edge at a first outer leaflet point, thereby forming a first baseline extending from the first outer leaflet point to the commissure, the first baseline further having a first width as measured from the first outer leaflet point to the commissure. Further, the second fan edge may intersect the second sinus edge at a second outer leaflet point, thereby forming a second baseline extending from the second outer leaflet point to the commissure, the second baseline further having a second width as measured from the second outer leaflet point to the commissure. In addition, the second baseline may be essentially collinear with the first baseline. The first sinus edge may also extend from and may not be coextensive with the first baseline, thereby forming a first sinus structure bounded by the first sinus edge, the commissure, and the first baseline, and the second sinus edge may extend from and may not be coextensive with the second baseline, thereby forming a second sinus structure bounded by the second sinus edge, the commissure, and the second baseline. Further, the first fan edge may extend from and may not be coextensive with the first baseline, thereby forming a first fan structure bounded by the first fan edge, the commissure, and the first baseline, and the second fan edge may extend from and may not be coextensive with the second baseline, thereby forming a second fan structure bounded by the second fan edge, the commissure, and the second baseline. Additionally, at least a portion of the first fan edge, at least a portion of the second fan edge, and at least a portion of the inner conduit surface may be mutually disposed to form a valve gap. Further, at least a portion of the first sinus structure and a portion of the inner conduit surface may be nonadjacent, thereby forming a first valve sinus bounded at least in part by at least a portion of the inner conduit surface and at least a portion of the first sinus structure, and at least a portion of the second sinus structure and a portion of the inner conduit surface may be nonadjacent, thereby forming a second valve sinus bounded at least in part by at least a portion of the inner conduit surface and at least a portion of the second sinus structure.

In an embodiment, a method of manufacturing a hybrid tissue-engineered valved conduit includes providing a heart valve structure having a conduit comprising a conduit wall, an inner conduit surface, an outer conduit surface, and a diameter, and a heart valve multi-leaflet structure, forming at least one conduit breach through the conduit wall, the at least one conduit breach having two conduit breach edges, providing at least one biodegradable structure having at least two sides, affixing a first biodegradable structure side to a first conduit breach edge, and affixing a second biodegradable structure side to a second conduit breach edge. The heart valve multi-leaflet structure may include a first heart valve leaflet, having a first sinus edge and a first fan edge, and a second heart valve leaflet, having a second sinus edge and a second fan edge, in which the first fan edge may intersect the second fan edge at an outer commissure point, and the first sinus edge may intersect the second sinus edge at an inner commissure point, thereby forming a commissure extending from the outer commissure point to the inner commissure point. Additionally, the first fan edge may intersect the first sinus edge at a first outer leaflet point, thereby forming a first baseline extending from the first outer leaflet point to the commissure, the first baseline further having a first width as measured from the first outer leaflet point to the commissure. Further, the second fan edge may intersect the second sinus edge at a second outer leaflet point, thereby forming a second baseline extending from the second outer leaflet point to the commissure, the second baseline further having a second width as measured from the second outer leaflet point to the commissure. In addition, the second baseline may be essentially collinear with the first baseline. The first sinus edge may also extend from and may not be coextensive with the first baseline, thereby forming a first sinus structure bounded by the first sinus edge, the commissure, and the first baseline, and the second sinus edge may extend from and may not be coextensive with the second baseline, thereby forming a second sinus structure bounded by the second sinus edge, the commissure, and the second baseline. Further, the first fan edge may extend from and may not be coextensive with the first baseline, thereby forming a first fan structure bounded by the first fan edge, the commissure, and the first baseline, and the second fan edge may extend from and may not be coextensive with the second baseline, thereby forming a second fan structure bounded by the second fan edge, the commissure, and the second baseline. Additionally, at least a portion of the first fan edge, at least a portion of the second fan edge, and at least a portion of the inner conduit surface may be mutually disposed to form a valve gap. Further, at least a portion of the first sinus structure and a portion of the inner conduit surface may be nonadjacent, thereby forming a first valve sinus bounded at least in part by at least a portion of the inner conduit surface and at least a portion of the first sinus structure, and at least a portion of the second sinus structure and a portion of the inner conduit surface may be nonadjacent, thereby forming a second valve sinus bounded at least in part by at least a portion of the inner conduit surface and at least a portion of the second sinus structure.

DETAILED DESCRIPTION

Figure 1:
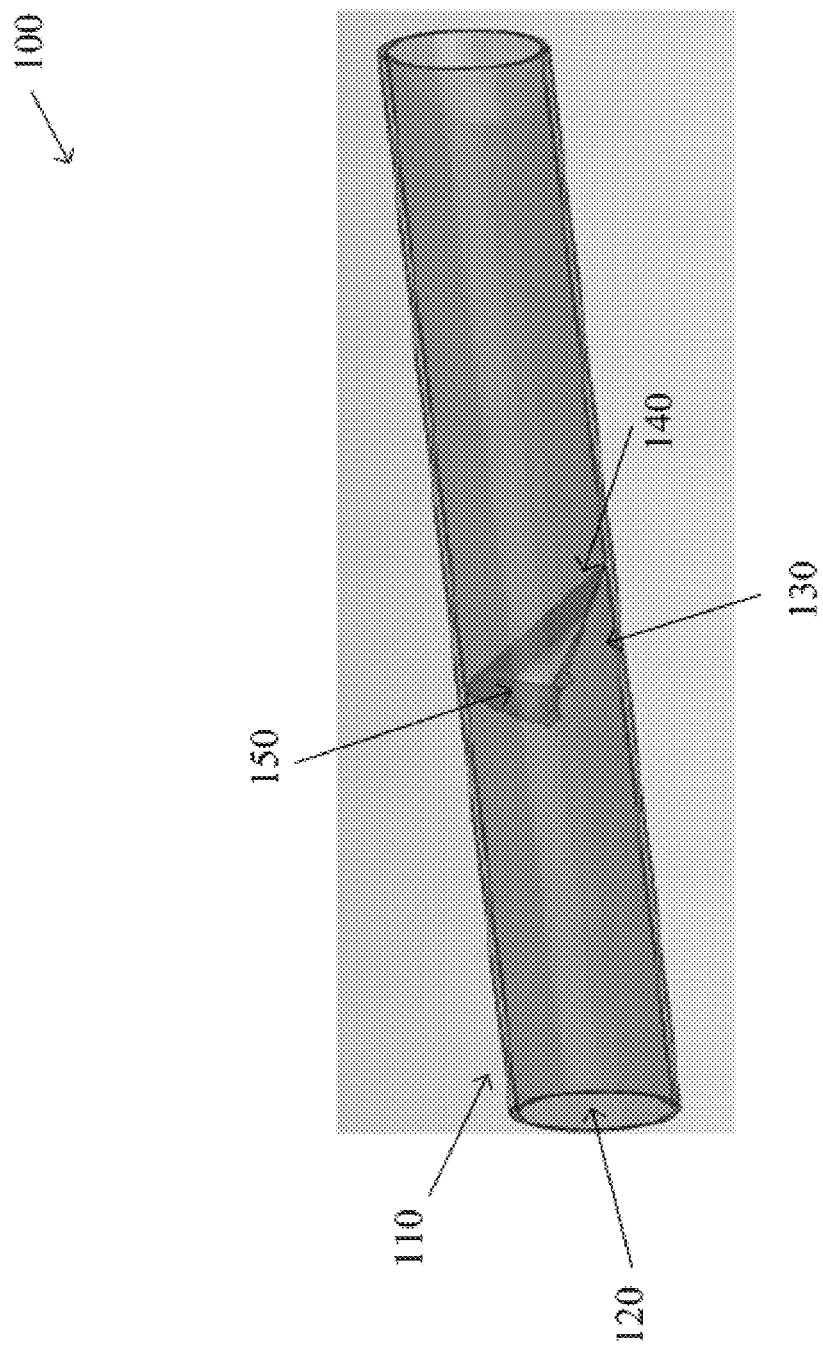
FIG. 1 illustrates an embodiment of a heart valve leaflet structure within a conduit.

FIG. 1 illustrates an embodiment of an artificial heart valve structure 100 that may be used, in a non-limiting example, as a shunt for connecting of the right ventricle to the pulmonary artery following a Norwood operation, as frequently performed for the treatment of hypoplastic left heart syndrome. In one non-limiting example, the artificial heart valve structure 100 may be indicated for the correction or reconstruction of the right ventricle outflow tract (RVOT) in pediatric patients. Such reconstruction may be indicated for congenital heart disorders such as tetralogy of Fallot, Truncus Arterious, Dextro-Transposition of the Great Arteries, Pulmonary Atresia of Intact Ventricular Septum, or Aortic Valvular Disease. Such an artificial heart valve structure 100 may also be indicated for the replacement of previously implanted homografts or valved conduits that have become dysfunctional or insufficient. In addition, the artificial heart valve structure 100 may have applications in treating a wider range of heart disorders, including other areas of the heart.

In one embodiment, an artificial heart valve structure 100 may include a generally tubular flexible conduit 110 containing a heart valve leaflet structure 130. In one embodiment, a heart valve leaflet structure 130 may be a heart valve single leaflet structure. In another embodiment, the heart valve leaflet structure 130 may be a heart valve multi-leaflet structure. A conduit 110 may be characterized as having a wall with an inner conduit surface 120, an outer conduit surface, and a diameter. In one non-limiting example, a conduit 110 may have a size less than or about 12 mm. In another non-limiting example, a conduit 110 may have a size greater than about 12 mm. In a non-limiting example, a heart valve leaflet structure 130 may include at least one generally triangular shaped fan structure 150, and may be located along the minor curvature along the inner surface 120 of conduit 110. In one non-limiting example, a heart valve leaflet structure may have extensions such as "wings" along one or more sinus structures, to allow for the placement of additional means of connection to the conduit inner surface. A heart valve leaflet structure 130 may have one or more sinus edges 140 fixed to the inner surface 120 of a conduit 110, and one or more fan structures 150 that can take on either an open or closed position with respect to the inner surface 120 of the conduit 110. In another non-limiting example, the one or more sinus edges 140 may have a fan shape.

In one embodiment, the conduit 110 and/or heart valve leaflet structure 130 may be made from a biocompatible and hemocompatible polymer. In one non-limiting embodiment, the polymer may be a fluoropolymer. Non-limiting examples of such biocompatible and hemocompatible polymers may include polytetrafluoroethylene, expanded polytetrafluoroethelyne, polyester, polyethylene terephthalate, polydimethylsiloxane, polyurethane, and/or combinations of those materials. In another embodiment, a conduit 110 and/or heart valve leaflet structure 130 may be made of a polymer coated with at least one bioactive coating. In still another embodiment, a conduit 110 and/or heart valve leaflet structure 130 may be surface-modified to include a bioactive material. In one non-limiting embodiment, a bioactive coating may be an anti-coagulant coating or a surface treatment to promote biocompatibility. Non-limiting examples of an anti-coagulant coating may include a coumarin, heparin, a heparin derivative, a Factor Xa inhibitor, a direct thrombin inhibitor, hementin, sintered porous titanium microspheres, and/or combinations of those materials.

The material from which a heart valve leaflet structure 130 may be fabricated may have a thickness of about 0.05 mm to about 0.2 mm. In one non-limiting embodiment, a heart valve leaflet structure 130 may be cut out of the material by hand, or with a hand-held tool. In one embodiment, a heart valve leaflet structure 130 may be cut out with a laser-cutter. In one embodiment, the heart valve leaflet structure 130 may be produced using a 3D printer and/or similar polymer injection devices. In one non-limiting example, a conduit 110 may have a thickness of about 0.5 mm to about 1 mm. In another non-limiting example, a conduit 110 may also have a diameter of about 8 mm to about 24 mm.

The sinus edge 140 of a heart valve leaflet structure 130 may be affixed to the inner surface 120 of a conduit 110. In one non-limiting example, the sinus edge 140 may be affixed by suturing. In another non-limiting example, a sinus edge 140 may be affixed via a bonding method such as laser welding, chemical welding, gluing, and/or suturing.

Figure 2:
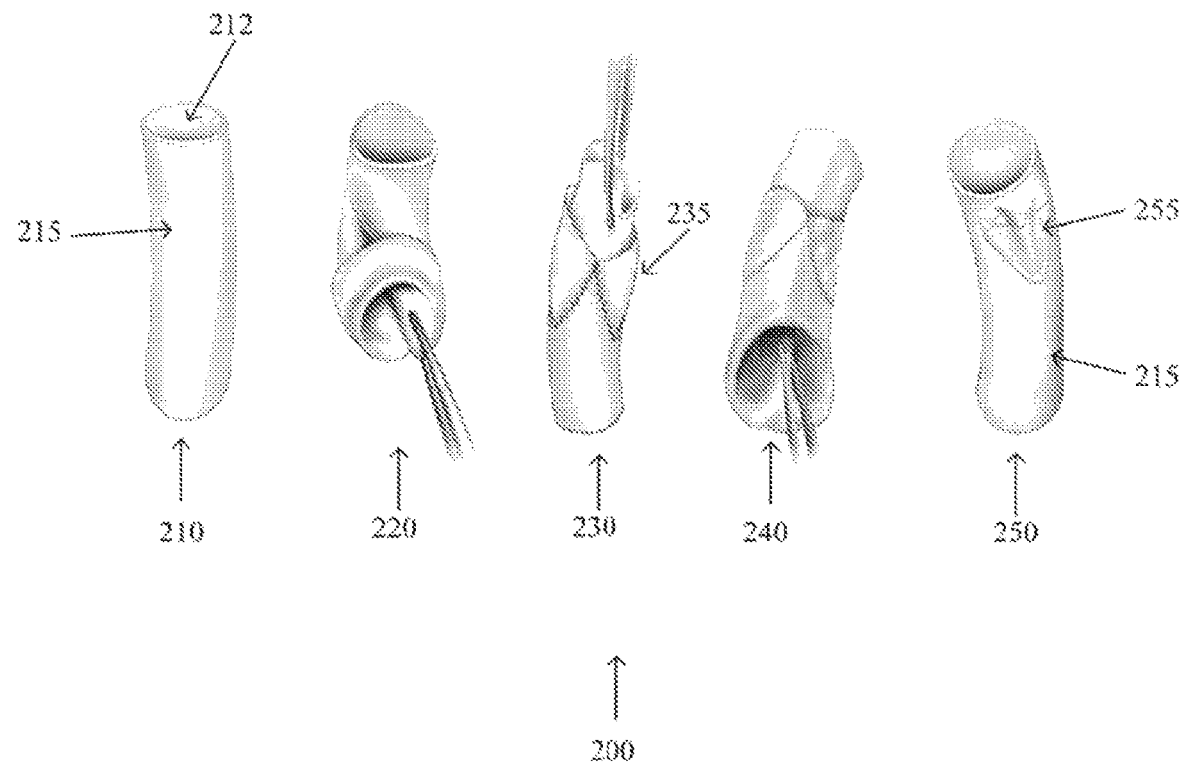
FIG. 2 illustrates a method of fabricating a heart valve structure in accordance with the present disclosure.

FIG. 2 illustrates an embodiment of a method 200 for fabricating an artificial heart valve structure. A flexible conduit may be provided 210 including a wall having an inner surface 212 and an outer surface 215. The conduit may then be everted 220, thereby providing access to the inner surface 212. One or more heart valve leaflet structures 235 may be provided that may be affixed 230 to the exposed inner surface 212. In one non-limiting embodiment, illustrated in FIG. 1, a heart valve leaflet structure may comprise one heart valve single leaflet structure. Alternatively, as illustrated in FIG. 2, multiple heart valve single leaflet structures 235 may be separately affixed to the exposed inner surface 212 of a conduit. In another alternative embodiment, a heart valve multi-leaflet structure may be so affixed.

As disclosed above, without limitation, one or more heart valve leaflet structures 235 may be affixed to a conduit inner surface 212 by suturing, chemical welding, heat welding, or gluing. In one non-limiting embodiment, a heart valve leaflet structure may be provided by applying a heart valve leaflet structure stencil, having essentially the same measurements as the final heart valve leaflet structure, to a material. One or more marks may be made on the material to essentially follow the heart valve leaflet structure stencil. A user may use a means to cut out or extract a heart valve leaflet structure from the material based at least in part on the markings made on the material.

In one embodiment, one or more heart valve leaflet structures 235 may be positioned against the inner surface 212 by eye prior the heart valve leaflet structures being affixed to the inner surface. In an alternative embodiment, a sinus stencil may be provided. A sinus stencil may be used by a fabricator as a template for marking the inner surface 212, thereby providing proper placement and alignment of one or more heart valve leaflet structures 235. The marking on the conduit inner surface 212 may be substantially the same as the sinus stencil. One or more sinus edges of one or more heart valve leaflet structures 235 may then be affixed to the conduit along the shape marked on the inner surface 212.

In one embodiment, a sinus stencil may have identical shape, size and/or dimensions as one or more heart valve leaflet structures 235. In an alternative embodiment, the sinus stencil may have a shape, size, and/or dimensions that differ from the shape, size, and/or dimensions of the one or more heart valve leaflet structures 235. Although FIG. 2 illustrates affixing one or more heart valve single leaflet structures to the inner surface 212 of the conduit, it may be appreciated that other, more complex, heart valve leaflet structures may be similarly affixed.

Once the one or more heart valve leaflet structures 235, have been affixed to the inner surface 212 of the conduit, the conduit may be reverted 240. The final heart valve structure may thus be formed 250 having the one or more heart valve leaflet structures 255 on the interior of the conduit, and the outer surface 215 of the conduit being disposed at the exterior of the conduit.

Figure 3A:
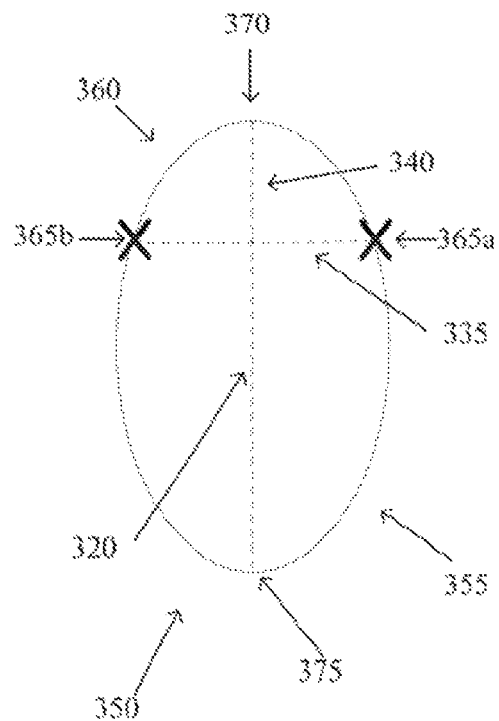
FIG. 3A illustrates an embodiment of a heart valve leaflet structure having a single leaflet composed of a sinus edge having one component in accordance with the present disclosure.
Figure 3B:
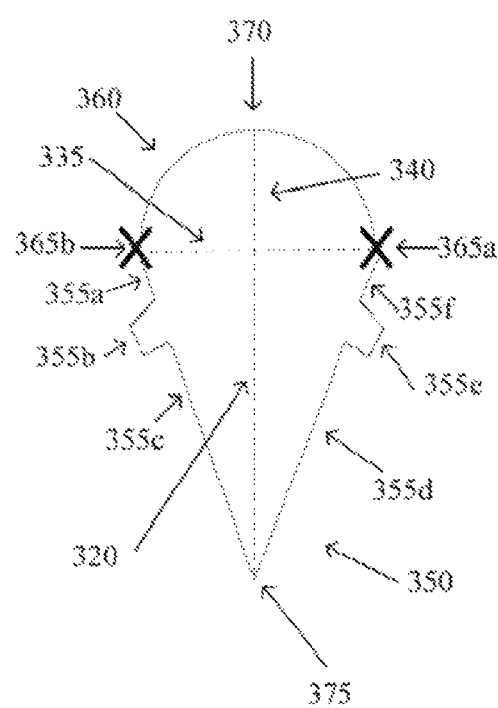
FIG. 3B illustrates an embodiment of a heart valve leaflet structure having a single leaflet composed of a sinus edge having multiple components in accordance with the present disclosure.

A heart valve leaflet structure as illustrated in FIG. 1 may include a number of components. FIGS. 3A and 3B illustrate two embodiments of a heart valve single leaflet structure 350. A heart valve leaflet structure may include a sinus edge 355 and a fan edge 360 that may intersect at one or more outer leaflet points 365a,b. In one embodiment, a baseline 335 may be defined as a line essentially joining the outer leaflet points 365a,b. In one embodiment, a baseline 335 may thus divide the heart valve leaflet structure 350 into two portions: a fan structure (bounded at least by the fan edge 360 and the baseline 335), and a sinus structure (bounded at least by the sinus edge 355 and the baseline 335).

Several metrics may be applied to the heart valve leaflet structure 350. For example, a fan structure may have a fan structure height 340 as measured from a maximal point 370 on the fan edge 360 that is most distal from the baseline 335, to the baseline. It may be appreciated that a fan edge 360 coextensive with its repsective baseline 335 may have effectively no fan structure height 340. Therefore, an embodiment of a heart valve leaflet structure having a fan structure may have at least a portion of the fan edge 360 non-coextensive with the baseline 335. A sinus structure may also have a height 320 measured from a maximal point 375 on the sinus edge 355 most distal from the baseline 335, to the baseline. It may further be appreciated that a sinus edge 355 coextensive with its respective baseline 335 may have effectively no height 320. Therefore, an embodiment of a heart valve leaflet structure having a sinus structure may have at least a portion of the sinus edge 355 non-coextensive with the baseline 335. The baseline 335 may also have a width as measured between the outer leaflet points 365a,b.

It may be appreciated that either one or both of the sinus edge 355 and/or the fan edge 360 may be composed of multiple components. For example, as illustrated in FIG. 3B, a sinus edge 355 may be composed of several components 355a-f. In some non-limiting examples, the components may be essentially straight lines, such as 355a,c,d,f. In some other non-limiting examples, sinus edge components may have more complex shapes such as "wings" 355b and 355e in FIG. 3B. It may also be appreciated that the maximal point of a sinus edge 375 may occur at the intersection of two sinus edge components (for example, the intersection of 355c and 355d), which may conveniently be termed a "sinus intersection".

Figure 3C:
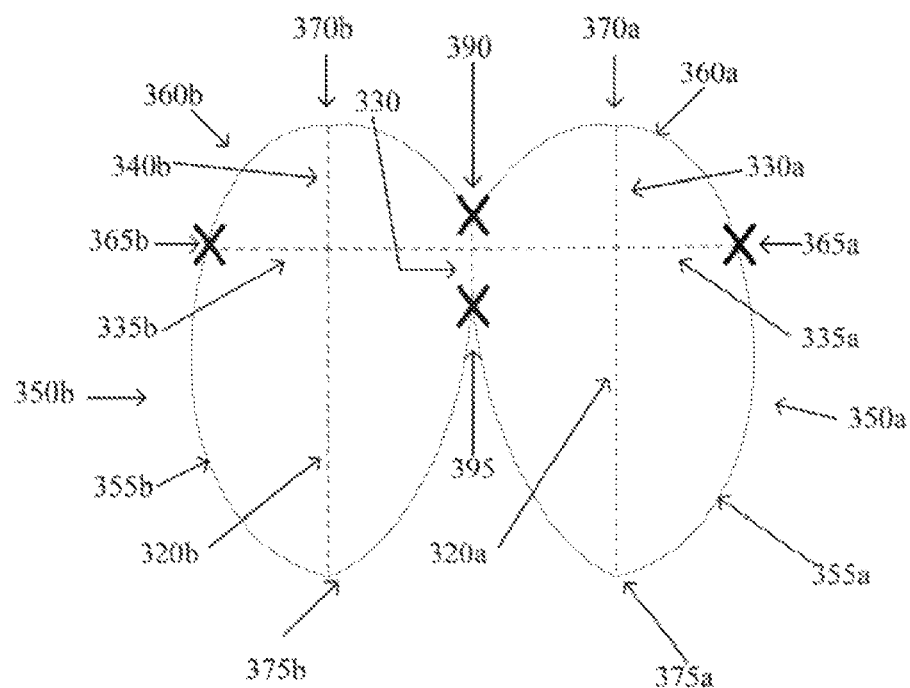
FIG. 3C illustrates an embodiment of a heart valve leaflet structure having multiple leaflet structures each composed of a sinus edge having one component in accordance with the present disclosure.

It may be appreciated that a heart valve leaflet structure may be composed of a number of leaflets. FIG. 3C illustrates one non-limiting example of a heart valve multi-leaflet structure composed of two heart valve leaflets, 350a,b. Many of the components in FIG. 3C may be found in FIGS. 3A and 3B. Thus there may be two sinus edges (375a,b), two fan edges (360a,b), two fan maximal points (370a,b), each defining a fan height (340a,b), and two sinus maximal points (375a,b), each defining a height (320a,b).

In addition, the two leaflets (350a,b) may be joined at their respective edges. Thus, the two fan edges (360a,b) may intersect at a point 390 that may be termed an outer commissure point, and the two sinus edges (355a,b) may intersect at a point 395 that may be termed an inner commissure point. A commissure 330 may thus be defined as a structure effectively bounded at least by the inner commissure point 395 and the outer commissure point 390. The commissure 330 may be characterized by a commissure length. An embodiment of a two-leaflet heart valve structure illustrated in FIG. 3C may be considered to have two baselines (335a,b), one baseline associated with each respective leaflet (350a,b). Each baseline (335a,b) may be characterized by a width as measured from an outer leaflet point (365a,b) to the commissure, 330. The two baselines 335a,b may also be essentially collinear. As disclosed above, with respect to the embodiment illustrated in FIG. 3A, a fan structure may be that portion of the leaflet 350 bounded at least by a fan edge 360 and a baseline 335. It may be appreciated that a fan structure of either one or both heart valve leaflets 350a,b in a two-leaflet heart valve structure may also be bounded at least by a portion of a commissure 330 in addition to the respective fan edges (360a,b) and baselines (335a,b). Similarly, it may be appreciated that a sinus structure of either or both heart valve leaflets 350a,b in a two-leaflet heart valve structure may be bounded at least by a portion of a commissure 330 in addition to the respective sinus edges (375a,b) and baselines (335a,b).

It may also be appreciated that a heart valve multi-leaflet structure may not necessarily include all the features as disclosed above with respect to FIG. 3C. In one non-limiting alternative embodiment, a heart valve multi-leaflet structure may have a commissure 330 essentially lacking a length. In such an embodiment, the inner commissure 395 point may essentially be coextensive with the outer commissure point 390.

It may be understood, with reference to the method illustrated in FIG. 2, that one or more sinus edges 355a,b of the one or more heart valve leaflets 350a,b may serve as at least a portion of points of attachment between the heart valve leaflets and the inner surface of a conduit. It may also be appreciated that at least a portion of a commissure 330 may also be affixed to the inner surface of a conduit.

Although FIGS. 3A-C illustrate embodiments of heart valve leaflet structures composed of one or two leaflets, it is understood that a heart valve leaflet structure may be composed of any number of leaflets. For example, a heart valve three-leaflet or four-leaflet structure may also be considered. By extension of the heart valve leaflet structure illustrated in FIG. 3C, a heart valve three-leaflet structure may comprise three leaflets, each leaflet having one or more of a sinus edge, a sinus structure, a fan edge, a fan structure, a baseline, a height, and a fan structure height. Such a three-leaflet structure may include, in one embodiment, two commissures: one commissure between a first leaflet and a second leaflet, and a second commissure between the second leaflet and a third leaflet. Each commissure may have a commissure length. Outer and inner commissure points equivalent to 390 and 395, respectively, may be also be defined between each pair of adjacent leaflets.

It may be further appreciated that equivalent metrics describing each leaflet of a multi-leaflet heart valve leaflet structure may differ. In one non-limiting embodiment, one leaflet may have a height that may differ from the height of any one or more other leaflets composing the multi-leaflet heart valve leaflet structure. In another non-limiting embodiment, one leaflet may have a sinus edge having a different perimeter length than the sinus edge perimeter length of one or more other leaflets. In yet another non-limiting embodiment, the sinus edge shape of one leaflet may differ from the sinus edge shape of one or more other leaflets. In still another non-limiting example, a fan structure shape of one leaflet may differ from the fan structure shape of one or more other leaflets.

Alternatively, some leaflets may have equivalent metrics that have about the same metric values. Thus, in one non-limiting example, some or all of the leaflets in a multi-leaflet heart valve leaflet structure may have baselines having about the same width. In another one non-limiting example, some or all of the leaflets in a multi-leaflet heart valve leaflet structure may have heights having about the same length.

Figure 3D:
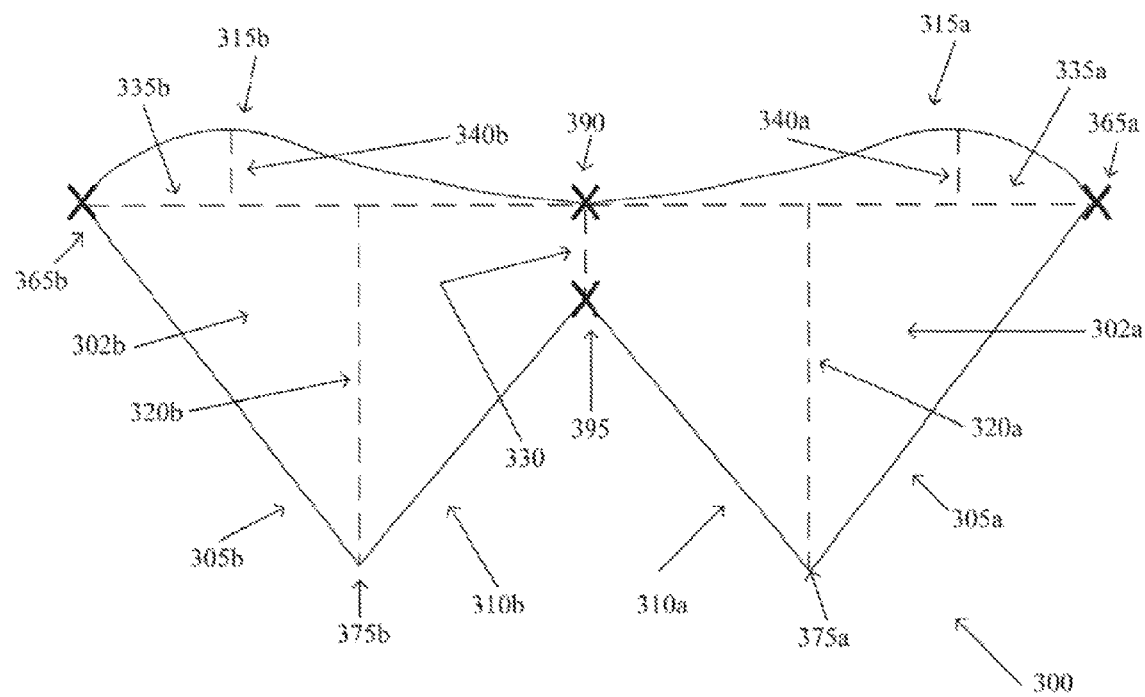
FIG. 3D illustrates an embodiment of a heart valve leaflet structure having multiple leaflets, each composed of a sinus edge having multiple components in accordance with the present disclosure.

Another embodiment of a heart valve multi-leaflet structure 300 is illustrated in FIG. 3D. A heart valve multi-leaflet structure 300 may include a pair of heart valve leaflets, each having an essentially triangular sinus structure 302a and 302b. A sinus edge of each leaflet may be composed of a combination of two or more components, including, as non-limiting examples, an outer edge component (305a,b) plus a respective inner edge component (310a,b). In addition, each heart valve leaflet may have a fan structure 315a and 315b. One end of a fan edge may intersect an end of its respective outer edge component, 305a,b, to form an outer leaflet point, 365a,b. In addition, the fan edge of one leaflet may intersect the fan edge of the second leaflet at an outer commissure point 390. Further the sinus edge of one leaflet may intersect the sinus edge of the second leaflet at an inner commissure point 395. With respect to the embodiment illustrated in FIG. 3D, an inner commissure point 395 may be found at an intersection of the first inner edge component 310a and the second inner edge component 310b. As disclosed above with respect to FIG. 3C, a commissure 330 may be defined as the portion bounded at least by the outer commissure point 390 and the inner commissure point 395.

As disclosed above with respect to FIG. 3C, each leaflet may have a baseline 335a,b, having a width measured between the respective baseline outer leaflet point 365a,b and a commissure 330. Further, each inner edge component 310a and 310b and each outer edge component 305a and 305b may be characterized by a length. Each leaflet may also have a sinus intersection (375a,b) located essentially at the intersection between an inner edge component (310a,b) and the respective outer edge component (305a,b). Additionally, each sinus structure may be characterized as having a height, 320a and 320b, measured from the respective base (335a,b) to the respective sinus intersection (375a,b). It may be appreciated that the sinus intersection of each leaflet (375a,b) may also be the maximal point on the respective sinus edge that is most distal from the respective baseline (335a,b).

It may be appreciated that metrics associated with one heart valve leaflet may be independent of another. Thus, the length of leaflet inner edge component 310a may differ from the length of inner edge component 310b; the length of outer edge component 305a may differ from the length of outer edge component 305b; height 320a may differ from height 320b; the width of baseline 335a may differ from the width of baseline 335b; and fan structure height 340a may differ from fan structure height 340b. Alternatively, in one non-limiting embodiment, the length of inner edge component 310a may be substantially the same as the length of inner edge component 310b. In another non-limiting embodiment, the length of outer edge component 305a may be substantially the same as the length of out edge component 305b In another non-limiting embodiment, height 320a may be substantially the same as height 320b. In yet another non-limiting embodiment, the width of baseline 335a may be substantially the same as the width of baseline 335b. In still another non-limiting embodiment, fan structure height 340a may be substantially the same as fan structure height 340b.

The metrics associated with a heart valve leaflet structure may be scaled with respect to each other. In one non-limiting example, the ratio between the height of one leaflet, such as 320a (or 320b), and the width of the baseline of that leaflet, such as 335a (or 335b, respectively), may be about 0.41 to about 0.77. In another non-limiting example, the ratio between the inner edge component length of one leaflet, such as 310a (or 310b), and the width of the baseline of that leaflet, such as 335a (or 335b, respectively), may be about 0.44 to about 0.77. In still another non-limiting example, the ratio between a length of the commissure 330 and the width of the base of one leaflet, such as 335a (or 335b), may be about 0.18 to about 0.38. In addition, metrics associated with a heart valve leaflet structure may be scaled with respect to a metric associated with a conduit to which it may be affixed. In one non-limiting example, the ratio between the width of the baseline of a leaflet, such as 335a or 335b, and the diameter of the conduit may be of about 0.054 to about 0.17.

While the sinus structure 302a,b of a heart valve leaflet as illustrated in FIG. 3D may be of a generally triangular shape, it may be appreciated that the sinus structure may also encompass alternative shapes. Thus, embodiments of the sinus structure 302a,b may include, without limitation, a generally quadrilateral shape, any closed multi-lateral shape, curved shapes, oval shapes, or other geometric shapes that may provide a sinus edge having one or more components that may be affixed to the inner surface of a conduit.

Each fan structure 315a and 315b may have any type of angular, linear, or curved fan edge. In one non-limiting example, each fan structure, 315a and 315b, may have a lobular edge, each lobular fan structure characterized by a fan structure height, 340a and 340b, measured from the maximal point of each fan edge to its respective base, 335a and 335b. In one non-limiting embodiment, a fan structure, 315a or 315b, may be essentially bilaterally symmetric. In another embodiment, fan structure 315a or 315b may be asymmetric and have an lobular edge composed of a steep portion proximate to an outer edge component (such as 305a or 305b) of the sinus edge of its respective heart valveleaflet (350a or 350b), and a shallow portion proximate to the outer commissure point 390. In another embodiment, fan structure 315a of one leaflet may be essentially mirror-image symmetric to fan structure 315b with respect to the commissure. In another embodiment, fan structure 315a may be essentially identical to fan structure 315b. In yet another embodiment, fan structure 315a may differ from fan structure 315b in edge shape, edge perimeter length, fan structure area, or in other metrics.

The dimensions of a fan structure, 315a and 315b, may be scaled with respect to other dimensions of a heart valve multi-leaflet structure. In one non-limiting example, the ratio between a fan structure height of one valve leaflet, such as 340a (or 340b), and the width of the baseline of that leaflet, such as 335a (or 335b, respectively), may be about 0.07 to about 0.14. While a fan structure, as disclosed above, may include an asymmetric single lobe disposed towards the outer edge component (305a,b) of the heart valve multi-leaflet structure, it may be appreciated that such a structure may be a non-limiting embodiment of a fan structure. Alternative fan structures may include one or more lobes, angles, and/or other geometries. Additional features may include symmetric or asymmetric distributions of such lobular, angular, or linear fan structures, which may appear along any one or more portions along a baseline.

Figure 3E:
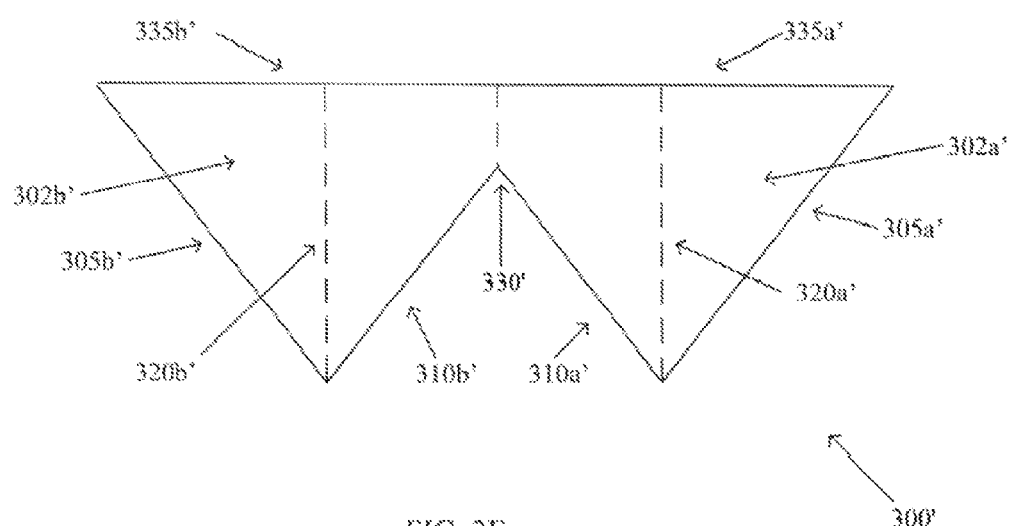
FIG. 3E illustrates an embodiment of a sinus stencil in accordance with the present disclosure.

As disclosed above, with respect to FIG. 2, a heart valve leaflet structure may be positioned on the inner surface 212 of an everted conduit by using a marking on the inner surface having a shape essentially similar to a sinus stencil. FIG. 3E illustrates an embodiment a sinus stencil 300' that may be used in conjunction with the heart valve multi-leaflet structure 300 illustrated in FIG. 3D. In one embodiment, a sinus stencil 300' may have the shape of two conjoined essentially triangular portions having coextensive bases, similar to the conjoined sinus structures 302a,b illustrated in FIG. 3D. In an embodiment, a sinus stencil 300' may lack one or more fan structures. In an alternative embodiment, a sinus stencil 300' may include one or more fan structures or portions of fan structures. In one non-limiting example, a sinus stencil 300' may include, for each sinus structure (302a and 302b), a sinus stencil outer edge component (305a' and 305b'), a sinus stencil inner edge component (310a' and 310b'), and a sinus stencil baseline (335a' and 335b'). Sinus stencil inner edge components, 310a' and 310b', may intersect essentially at the sinus stencil collinear bases (335a' and 335b'). Alternatively, sinus stencil inner edge components 310a' and 310b' may intersect at some point away from the collinear sinus stencil baselines, 335a' and 335b', thereby forming a sinus stencil commissure 330'. Each sinus stencil outer edge component (305a' and 305b') and inner edge component (310a' and 310b') may be characterized by a respective length. Further, each sinus stencil may be characterized by one or more heights (320a' and 320b'). Additionally, each sinus stencil baseline (335a' and 335b') may be characterized by a respective width. The sinus stencil commissure 330' may also be characterized by a sinus stencil commissure length.

It may be appreciated that metrics associated with a sinus stencil 300' may be about the same as or differ from the respective equivalent metrics associated with a heart valve leaflet structure 300. It may be understood that "respective equivalent metrics" may refer to measurements of equivalent components of a heart valve multi-leaflet structure 300 and a sinus stencil 300'. Thus a heart valve leaflet structure outer edge component 305b (or 305a) may be an equivalent component to a sinus stencil outer edge component 305b' (or 305a', respectively). A heart valve leaflet structure inner edge component 310b (or 310a) may be an equivalent component to a sinus stencil inner edge component 310b' (or 310a', respectively). A heart valve leaflet structure height 320b (or 320a) may be an equivalent component to a sinus stencil height 320b' (or 320a', respectively). A heart valve leaflet structure baseline 335b (or 335a) may be an equivalent component to a sinus stencil baseline 335b' (or 335a', respectively). A heart valve leaflet structure commissure 330 may be an equivalent component to a sinus stencil commissure 330'.

Although FIG. 3E illustrates a sinus stencil 300' having two sinus structures 302a' and 302b', it may be appreciated that a sinus stencil may be composed of any number of sinus structures. It may be appreciated that the number of sinus structures, 302a' and 302b', of a sinus stencil 300' may correspond to the number heart valve leaflets 350a,b of a heart valve leaflet structure 300 with which it may be used. A heart valve leaflet structure 300 composed of a single or multiple leaflets (for example three leaflets) may have an equivalent sinus stencil 300' composed of the same number of sinus structures. Thus, a heart valve leaflet structure 300 having a single leaflet may have an equivalent sinus stencil 300' having a single sinus structure, while a heart valve leaflet structure having three leaflets (as a non-limiting example) may have an equivalent sinus stencil having three sinus structures.

Once a heart valve multi-leaflet structure has been properly positioned on the inner surface of an everted conduit, the heart valve multi-leaflet structure may be affixed to the conduit as disclosed above in FIG. 2, 230. In one non-limiting embodiment, a heart valve multi-leaflet structure may be affixed to a conduit along at least a portion of the sinus edge. In the embodiment illustrated in FIG. 3D, a portion of the sinus edge may include any portion or portions along the combination of the outer edge component 305a (or 305b) plus inner edge component 310a (or 310b) of the respective leaflets. In another embodiment, a heart valve multi-leaflet structure may also be affixed to the inner surface at least along a portion of the commissure 330. Once a heart valve multi-leaflet structure has been properly affixed to the inner surface of the conduit, the conduit may be reverted, (FIG. 2, 240).

As disclosed above, any one or more of the metrics associated with a sinus stencil 300' may be about the same as or differ from the respective equivalent metrics of a heart valve multi-leaflet structure 300. In one non-limiting embodiment, the metrics associated with a heart valve multi-leaflet structure 300 may be about the same as the respective equivalent metrics associated with the sinus stencil 300'. For such an embodiment, it may be appreciated that sinus structures 302a and 302b may be lying essentially against and effectively contacting the inner surface of the conduit.

In another non-limiting embodiment, one or more metrics associated with a heart valve single leaflet or multi-leaflet structure 300 may be larger than the respective equivalent metrics associated with a sinus stencil 300'. As one non-limiting example, an inner edge component of a heart valve multi-leaflet structure (310a, for example) may have a length of about 8.1 mm, while the length of the equivalent inner edge component of the sinus stencil (310a', for example) may be about 7.7 mm. For such an embodiment, it may be appreciated that at least a portion of sinus structures 302a and 302b may be nonadjacent to the inner surface of a conduit. Thus, some portion of sinus structures 302a and 302b may be unattached to and have no or minimal contact with a conduit inner surface; however, some other portion of the sinus structures may be directly attached to and in effective contact with a conduit inner surface. The portion of sinus structures 302a and 302b that may be directly attached to and be in contact with a conduit inner surface may include at least some portion of the sinus edges. At least some portion of sinus structures 302a and 302b may be puckered away from the inner surface of a conduit when a heart valve multi-leaflet structure is affixed to the inner surface of the conduit. This puckering effect may thereby produce a valve sinus bounded by at least some portion of a sinus structure (302a or 302b) and at least a portion of the inner surface of the conduit. Depending on the orientation of fan structures 315a,b with respect to the inner surface of a conduit, a valve sinus may also be in part bounded by at least a portion of fan structures 315a,b and/or baselines 335a,b.

Figure 4:
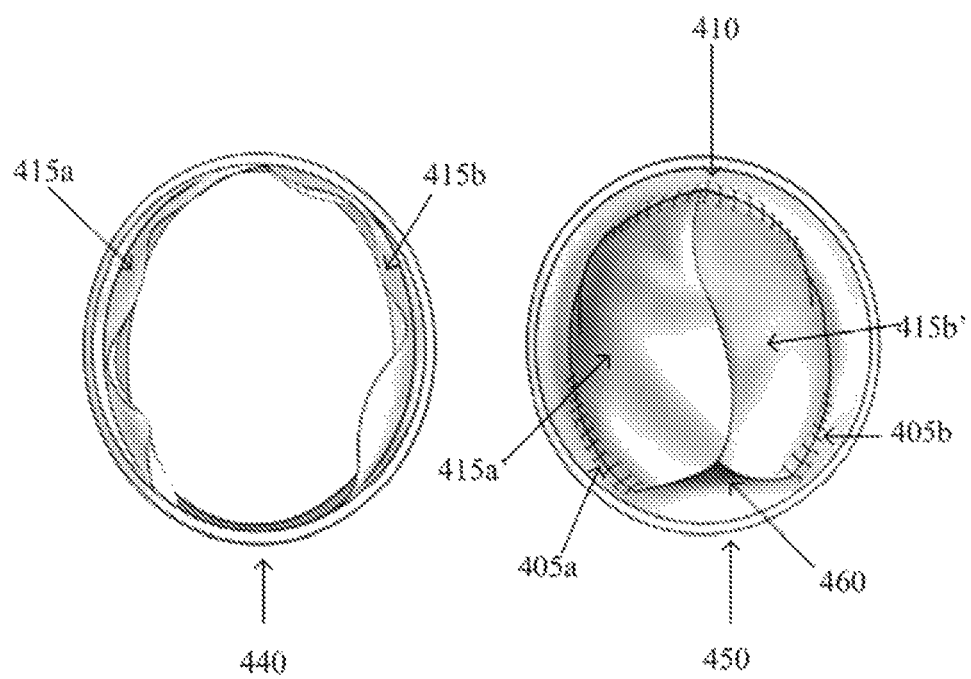
FIG. 4 illustrates an embodiment of a heart valve structure in accordance with the present disclosure.

FIG. 4 illustrates an interior downstream view of a heart valve structure in an open, 440, and closed, 450, configuration. In an open 440 configuration, blood may flow through the heart valve multi-leaflet structure, forcing fan structures 415a and 415b towards the inner surface of a conduit. In a closed configuration 450 fan structures 415a' and 415b' may form a closure against fluid backflow. In some non-limiting examples, lobes of fan structures 415a' and 415b' may be proximate, juxtaposed, and/or overlap in whole or in part. In some non-limiting examples, the closure may be planar, concave, and/or convex, or form an otherwise non-planar surface.

Closed configuration 450 further illustrates the relative locations of sutures or other means of affixing a heart valve multi-leaflet structure to the inner surface of a conduit. Specifically, inner edge components of two leaflet structures may be affixed as indicated by 410, while outer edge components of the two leaflet structures may be affixed as indicated by 405a and 405b. In one embodiment, a heart valve multi-leaflet structure and at least a portion of a conduit inner surface may be disposed to form a small gap 460 bounded by at least a portion of the inner surface of the conduit and a portion of the fan edge of each of fan structures. For a heart valve multi-leaflet structure in FIG. 4 corresponding to the embodiment of a heart valve multi-leaflet structure 300 in FIG. 3D, gap 460 may be bounded by the steep edges of fan structures 315a,b and the inner surface of a conduit. It may be understood that alternative heart valve multi-leaflet structures may include fan structures having fan edges with shapes differing from those disclosed above with respect to FIG. 3D. However, at least some portion of the fan edge of each such fan structure, when in closed configuration 450, may also form a gap 460 with the inner conduit surface.

Although FIG. 4 illustrates a heart valve structure having two leaflets, it may be appreciated that a heart valve structure may include any number of leaflets. Thus, a heart valve structure may incorporate a single leaflet, as illustrated in FIG. 1. Alternatively, a heart valve structure may incorporate a heart valve leaflet structure composed of three of more leaflets. In a non-limiting example, a heart valve structure may have three leaflets, the third leaflet positioned to cover gap 460 so as to essentially prevent regurgitative flow through the heart valve structure.

Figure 5:
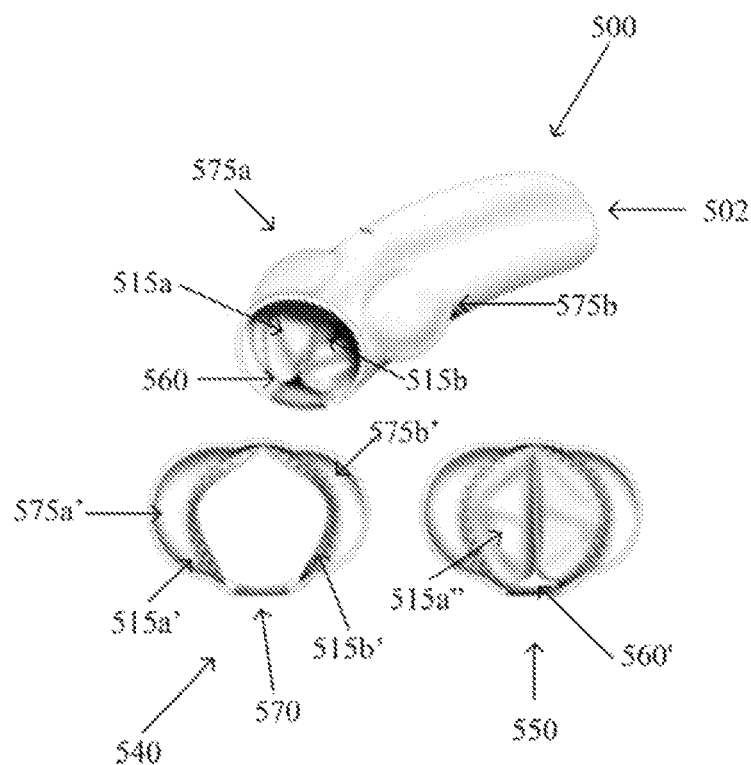
FIG. 5 illustrates an embodiment of an open and closed heart valve leaflet structure within a heart valve structure in accordance with the present disclosure.

FIG. 5 illustrates another embodiment of a heart valve structure. The top view 500 presents a partial cut-away view of a heart valve structure at a portion slightly downstream of the heart valve multi-leaflet structure (shown in a closed configuration). The upstream end 502 of a heart valve structure may be positioned in a patient's vasculature or cardiac structure to receive blood flowing to the heart valve structure. The closure of a heart valve structure may be formed from two fan structures 515a and 515b from a heart valve multi-leaflet structure. The closure may not be entirely closed to blood flow. In one embodiment, a small gap 560 may be formed by the mutual disposition of at least some portion of the fan edge of each of fan structures 515a and/or 515b and the inner surface of a conduit. In one non-limiting example, gap 560 may include about 15% of the circumference of a conduit inner surface.

Additional structures may also be present. In one embodiment, one or more conduit sinus structures 575a and 575b may also be present. Conduit sinus structures 575a and 575b may be formed by deformation of the conduit wall, and may be placed downstream of a heart valve multi-leaflet structure. Conduit sinus structures 575a and 575b may be generally concave with respect to the inner surface of the conduit. In one non-limiting example, conduit sinus structures 575a and 575b may be generally spheroidally concave. In another non-limiting example, conduit sinus structures 575a and 575b may be generally cubically concave. It may be understood that the outline and cross section of conduit sinus structures 575a and 575b may have any geometry as long as the conduit sinus structures maintain a concavity with respect to a conduit inner surface.

View 540 presents an embodiment of a heart valve structure in an open configuration, and 550 presents an embodiment of a heart valve structure in a closed configuration. In open configuration 540, fan structures 515a' and 515b' may be disposed in an extended downstream-pointing position. An interior concavity of each of the conduit sinus structures 575a' and 575b' may also be observed. In one embodiment, fan structures 515a' and 515b' while in the open configuration 540 may also extend into at least a portion of the conduit sinus structures 575a' and 575b'. In closed configuration 550, each fan structure (for example, 515a") of the heart valve multi-leaflet structure may be disposed in a neutral position In a neutral position, the two fan structures may be disposed with respect to each other as to form a nearly complete closure. In closed configuration 550, a small gap 560' may develop from the disposition of at least a portion of the fan edges (for example, the steep edge of each fan structure) and a conduit inner surface.

While FIG. 5 illustrates an embodiment of a two-leaflet heart valve structure, it may be appreciated that a heart valve structure may include additional heart valve leaflets. In one non-limiting example, a three-leaflet heart valve structure may be considered. Such a heart valve structure may incorporate a closure formed by the juxtaposition, proximity, and/or overlap of three fan structures. The mutual disposition of some portions of three fan edges along with the inner surface of the conduit may result in a gap structure similar to 560'. Alternatively, three fan structures may be disposed so that, effectively, no gap is formed.

Figure 6:
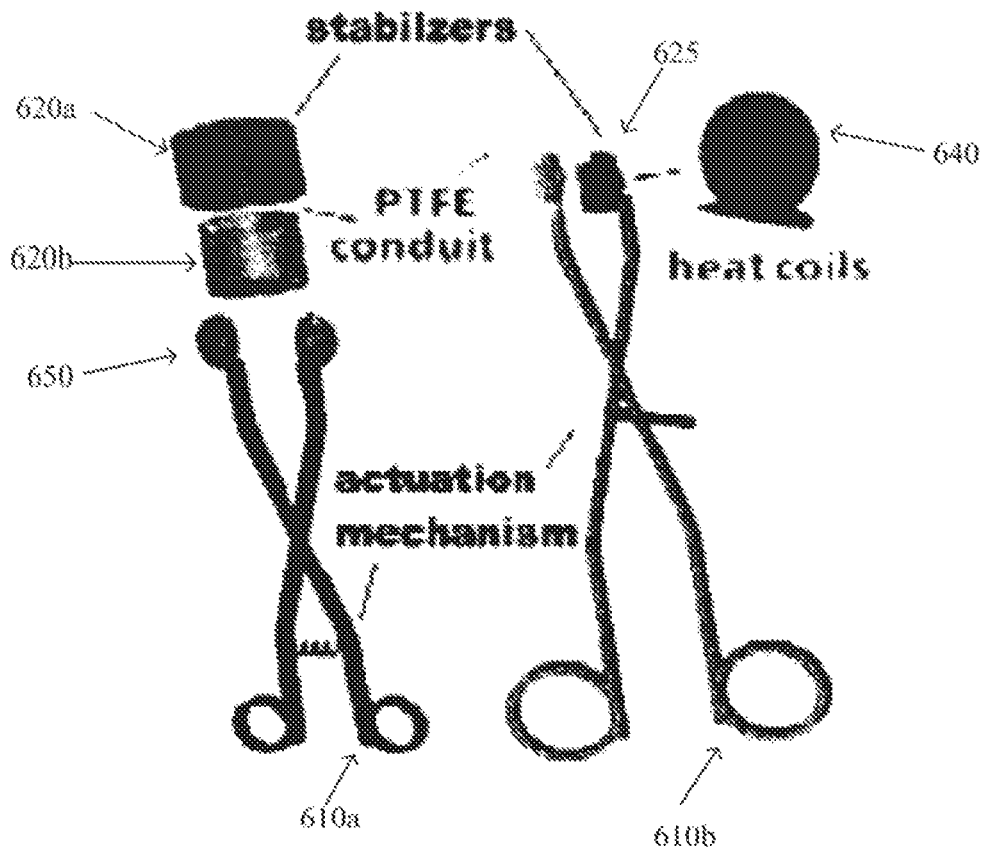
FIG. 6 illustrates embodiments of devices to form one or more conduit sinuses in a heart valve structure in accordance with the present disclosure.

One or more conduit sinus structures 575a and 575b may be formed from a conduit wall according to any method appropriate for deforming the conduit wall material. FIG. 6 illustrates non-limiting examples of conduit sinus fabrication devices 610a and 610b that may be used to form such conduit sinus structures. Examples of conduit wall deformation methods may include, without limitation, one or more of mechanical deformation (such as stretching or mechanical forming), heat forming, and/or vacuum forming. In one example, conduit sinus structure geometries may be created by a conduit sinus fabrication device 610a having a dome 650 that may have the shape of the desired conduit sinus geometry. A conduit sinus fabrication device 610a may deform the conduit material from the inside of a conduit via applied pressure and/or heat. Additionally, the portion of the conduit away from the domed portion 650 may be preserved by a semi-cylindrical mechanical stabilizer 625, or a cylindrical stabilizer 620a,b having components located inside and outside of a conduit. In one embodiment, a stabilizer 625 may contain an opening to allow the dome 650 and deformed conduit wall material to move while preventing movement of the conduit wall away from a conduit sinus structure. In one embodiment, an inner 620b stabilizer and an outer 620a stabilizer may be aligned manually by means of attachment to a conduit sinus fabrication device 610a and 610b. In another non-limiting embodiment, a conduit sinus fabrication device 610a and 610b may include magnets to help stabilize the conduit wall material. Non-limiting examples of a conduit sinus fabrication devices 610a and 610b may have the dome 650 actuated manually, by a potential energy device (such as a spring), or by magnets/electromagnets. In another non-limiting example, the dome 650 may be constructed from a thermally conductive material and heated by electric heating device 640 contained within the dome itself.

The shape and/or metrics associated with a heart valve multi-leaflet structure may be determined by a health care provider based on his or her experience and/or expertise. In an alternative embodiment, the shape and/or metrics associated with a heart valve leaflet structure may be determined, at least in part, based on calculations including, without limitation, mathematical modeling and/or optimization methods. In one non-limiting embodiment, customized heart valve leaflet structures may be fabricated for an individual patient. In another non-limiting embodiment, a 'standardized" heart valve leaflet structure may be fabricated that may be used by a number of patients who may not require a completely customized heart valve structure as a remedy for a pathology.

In one embodiment, modeling and/or optimization calculations may be used to reduce diastolic flow regurgitation through a heart valve structure, as well as to improve effective orifice area and overall heart valve structure function. In one non-limiting embodiment, a heart valve leaflet structure modeling program may predictively generate one or more heart valve leaflet structure models based at least on geometric parameters and solid-mechanics principals. In another non-limiting embodiment, one or more solid heart valve leaflet structure models may be analyzed according to one or more fluid flow analytical methods. Non-limiting examples of such fluid flow analytical methods may include fluid-structure interaction (FSI) and computational fluid dynamics (CFD) simulations. In a non-limiting embodiment, an iterative optimization method for generating heart valve leaflet structure models may include: (1) calculating a heart valve leaflet structure model based on a set of parameters including one or more geometric parameters; (2) analyzing a performance of the heart valve leaflet structure model based at least in part on one or more fluid flow analytical methods; (3) calculating a performance cost function according to data calculated by the one or more fluid flow analytical methods; and (4) varying one or more of the heart valve leaflet structure modeling parameters in a manner to minimize the value of the valve performance cost function.

Mathematical modeling and/or optimization calculations that may be used to calculate shapes and/or dimensions of heart valve leaflet structures may include, without limitation, computational fluid dynamics (CFD), solid-mechanics modeling, fluid/structure interaction (FSI) modeling, and blood-flow optimization algorithms. Calculations based on CFD models may show a difference in blood flow velocity based on a curvature of the conduit component of a heart valve structure. For example, a blood flow model may indicate greater flow along a conduit axis having a small radius of curvature as opposed to the blood flow in a conduit having a larger radius of curvature. CFD models, for example, may provide data to suggest that a curved conduit should not have a heart valve leaflet structure at the conduit bottom as a heart valve leaflet structure lower leaflet may become stuck at the closing phase, thereby leading to thrombosis.

Mathematical calculations and/or optimization calculations may be carried out, for example, by means of one or more computing devices. Such computing devices may include, without limitation, one or more of the following: central processor units, numerical accelerators, static and/or dynamic memories, data storage devices, data input devices, data output devices, communication interfaces, and visual displays. While a single computing device may be used for such calculations, multiple computing devices, for example in a shared network or cloud configuration, may also be used. It may be appreciated that the one or more computing devices may operate independently or in concert. In addition, communications between one or more users and one or more computing devices may occur over one or more input interface device, including, without limitation, a keyboard, a mouse, a track-ball, a stylus, a voice recognition system, and/or a touch pad display. In addition, the one or more computing devices may provide output information to the one or more users by one or more output interface device, including, without limitation, a visual display, a printer, and/or an audio interface. Data communication between computing devices may occur over one or more computing system communication interface, including, but not limited to, a serial interface, a parallel interface, an Ethernet interface, a wireless interface, and/or an optical interface. Additional communications between computing devices, or between computing devices and users, may be accomplished over one or more computing system communication protocols including, but not limited to, a personal area networks (such as BlueTooth), a local area network, a wide area network, and/or a satellite network.

Figure 7:
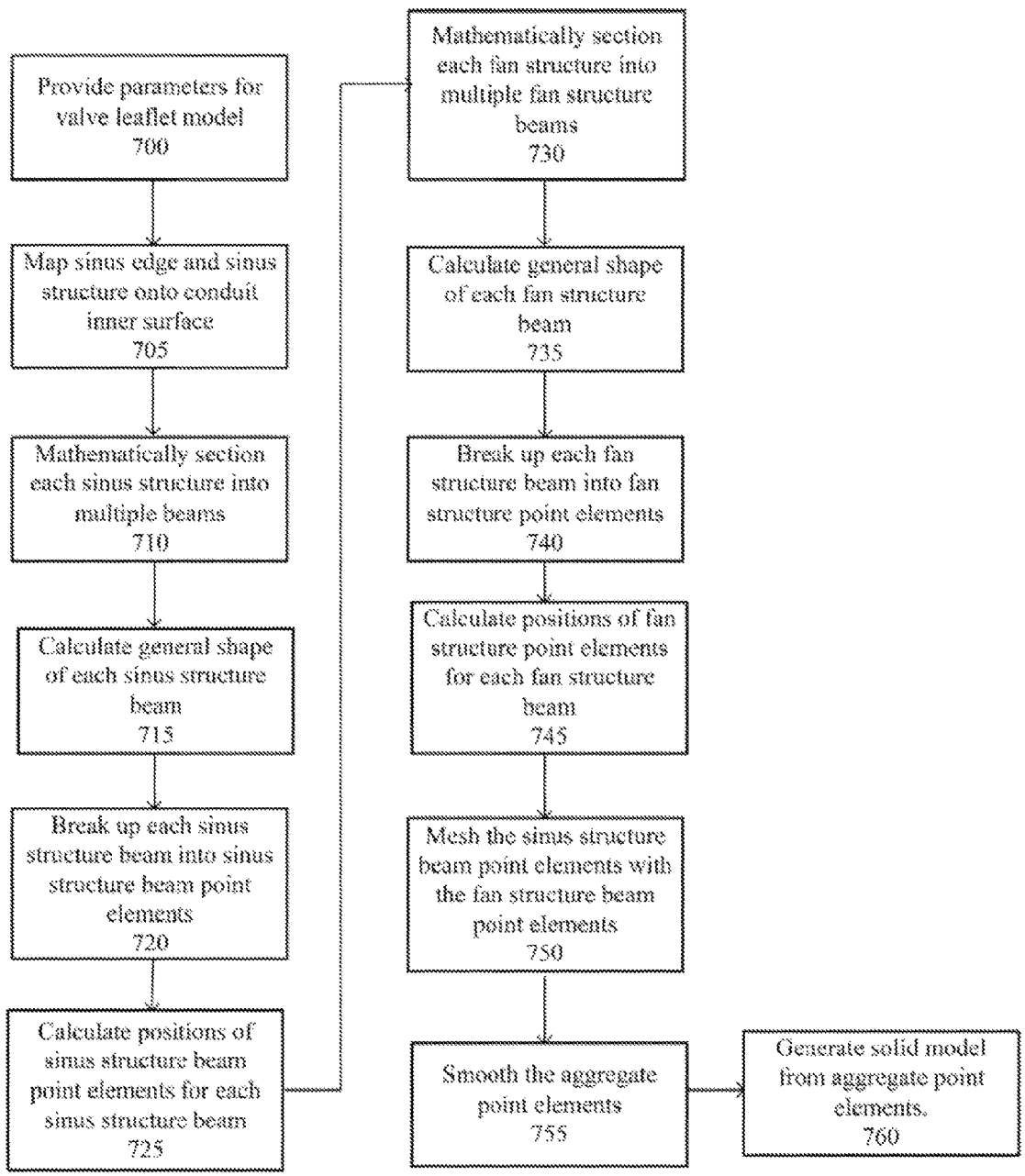
FIG. 7 is a flow chart of one embodiment of a method to provide a model of a heart valve leaflet structure in accordance with the present disclosure.

FIG. 7 is a flow chart illustrating an embodiment of a method for designing a heart valve leaflet structure.

Initially, leaflet modeling parameters may be provided to the heart valve leaflet structure model 700. Non-limiting examples of leaflet modeling parameters may include one or more of a sinus edge shape, a sinus edge perimeter length, a fan edge shape, a fan edge perimeter length, a height, a fan structure height, a baseline width, a commissure length, a modulus of elasticity of the heart valve leaflet structure material, a pressure across the heart valve leaflet structure, and a fluid flow rate through the heart valve leaflet structure. A leaflet structure modeling computation may then create initial two dimensional leaflet shapes.

Data provided to such leaflet structure modeling computation and optimization calculations, for example, may be used by such models and optimization calculations to calculate patient specific shapes and dimensions of heart valve leaflet structures and/or their related sinus stencils. In one embodiment, data used in the modeling and/or optimizing computer programs may include, without limitation, at least some physiological and/or anatomic data from a specific patient to receive a heart valve leaflet structure (as a customized device). In another embodiment, physiological and/or anatomical data from a number of individuals may be used either as aggregated raw data or as statistically analyzed data (e.g. mean values, variance values, and/or standard deviations) in modeling calculations for heart valve leaflet structures. In an embodiment, data may be derived from individuals sharing at least one characteristic with a patient, including without limitation, age, sex, height, weight, blood pressure, and degree of pathology (if any).

Sinus edges and sinus structures of a heart valve leaflet structure initial model may then be mapped onto the inner surface of a conduit model 705. A sinus stencil model may be used to map the sinus edge of the heart valve leaflet structure initial model onto the inner surface of a conduit model. Points composing the sinus edge may act as points of attachment to the inner surface of a conduit model; for convenience, such an attachment may be referred to as a "pinned" attachment. For the purpose of modeling a heart valve leaflet structure within a conduit, the flexibility of the sinus edge at the sinus edge points may result in negligible transferable moment from the pinned attachments through the sinus structure. In one embodiment of a mapping step, a heart valve leaflet structure model, including the sinus structures, may be assumed to be bilaterally symmetric with respect to a commissure.

The sinus structures may be sectioned into a finite number of thin, neighboring sinus structure beams 710. In one non-limiting embodiment, sinus structure beams may be created after the heart valve leaflet structure model has been mapped to the inner surface of a conduit model. In an alternative embodiment, sinus structure beams may be created as part of a heart valve leaflet structure initial model. The general shape of each beam (as a thin ribbon) may then be calculated 715. In one non-limiting embodiment, a mode of sinus structure beam deformation may be by buckling. A length of each sinus structure beam may be very long compared to its end-point-to-end-point distance after being affixed to the inner surface of a conduit. The very thin (0.1 mm) and flexible sinus structure beams may buckle easily and may not hold significant compressive strain. Strain between neighboring sinus structure beams may occur along the shape of the sinus structure. In one non-limiting embodiment, shape deformation between neighboring sinus structure beams may be ignored during modeling. In another non-limiting embodiment of a heart valve leaflet structure model, strain due to the weight of the heart valve leaflets may be neglected. As a non-limiting example, for a heart valve leaflet structure model based on a heart valve leaflet structure composed of expanded PTFE, the thin leaflets may have a very low weight compared to their elastic modulus, and therefore any strain induced by the weight of the leaflets may be ignored.

In one non-limiting example, a calculation may be performed according to a numerical multi-mode buckling analysis. Each sinus structure beam may undergo multiple interactions, both with the opposing leaflet and with the conduit inner surface. Many possible modes of buckling may be accounted for, both in-line and offset, including fixed-fixed (i.e. from one unattached sinus structure edge to another unattached sinus structure edge), pinned-pinned (i.e. from one sinus structure edge affixed to the conduit inner surface to another sinus structure edge affixed to the conduit inner surface), and pinned-fixed. In one non-limiting embodiment, these modes of buckling may be solved numerically. In a non-limiting embodiment, a multi-mode numerical buckling solver may be used.

A general solution to a beam undergoing buckling may be shown to be:

$$y = A \sin(kx) + B \cos(kx) + Cx + D \quad \text{(Eq. 1)}$$

where y may be the perpendicular distance from the original sinus structure beam at any given point. By finding the first and second derivatives of Eq. 1, the slope and moment may be shown to be:

$$y' = Ak \cos(kx) - Bk \sin(kx) + C \quad \text{(Eq. 2)}$$

$$y'' = -Ak^2 \sin(kx) - Bk^2 \cos(kx) \quad \text{(Eq. 3)}$$

at every point along the sinus structure beam. By imposing boundary conditions (such as $y_o'' = y_L'' = 0$ for a pinned-pinned sinus structure beam), and maintaining sinus structure beam length and overall continuity, a shape of the buckled sinus structure beam may be calculated. By maintaining continuity of the distance from a given point along a sinus structure beam to a fixed sinus edge before and after buckling, a three dimensional shape of the sinus structure beam may be found after buckling.

Where a solved sinus structure beam shape intersects a solid boundary, the intersection point may be assumed to be a vertex, so that segments before and after that vertex may undergo independent buckling while maintaining continuity between the two segments at the intersection point. This vertex point may then be iteratively varied along the boundary through an optimization routine. In one non-limiting embodiment, an optimization routine may include a vertex point cost function defined as the discrepancy at a vertex between an applied moment from a sinus structure beam side and an applied moment from a solid boundary side. Under an optimization condition, a discrepancy between the applied moments may approach about zero, since continuity may require that applied moments may be about equal. By iteratively applying this procedure for all intersections that arise, a final shape of each sinus structure beam may be calculated. In one non-limiting embodiment, the calculations may be simplified by assuming that sinus structure beam shapes at the symmetry line between heart valve leaflets may be linear. Results of modeling the sinus structures may include locations of the sinus structure edge pinned to the inner surface of a conduit model, and location of the baseline of the modeled sinus structure.

After a general shape of each beam has been calculated, each sinus structure beam may be further sectioned into a finite number of point-elements 720. A position of each of the sinus structure beam point elements may then be calculated 715. One or more position metrics for each sinus structure beam point-element may be calculated in accordance to a number of different methods. In one non-limiting example, a sinus structure beam point-element location may be calculated based at least in part on a change in its position along the sinus structure beam from its position along the initial sinus structure beam length. In another example, a distance may be calculated between individual sinus structure beam point-elements. In yet another example, a distance of each sinus structure beam point-element may be calculated from the maximal point of the relevant sinus edge or sinus intersection. In another example, a sinus structure beam point-element location may be adjusted to account for small amounts of strain in the leaflets.

After sinus structure beam point-element locations have been calculated, as disclosed above, each leaflet fan structure may be similarly modeled. A fan structure may initially have its baseline mapped to the baseline of its respective modeled sinus structure. In one non-limiting embodiment, a fan structure may be sectioned into a number of fan structure beams 730. In one embodiment, the fan structure beams may be created after the fan structure baseline has been mapped onto the modeled sinus structure baseline. In another embodiment, the fan structure beams may be created as part of a heart valve leaflet structure initial model. A general shape of each fan structure beam may then be calculated 735 according to modeling and optimizations calculations as substantially disclosed above with reference to the sinus structure beams. Thereafter, each fan structure beam may be sectioned into a number of fan structure beam point-elements 740, and one or more position of each fan structure beam point-element may be calculated in a manner substantially disclosed above 745 with respect to the sinus structure beam point-elements.

After the location of sinus structure beam point-elements and fan structure beam point-elements have been calculated, both sets of point-elements may be incorporated into a single set that may conveniently termed a "point-element aggregate". Point-elements composing the point-element aggregate may then be modeled by a point-element aggregate mesh representation 750. The point-element aggregate mesh representation may then be smoothed 755. In one non-limiting embodiment, the smoothing calculation may be derived from the use of Bezier curves.

Once a point-element aggregate mesh representation has been calculated, a solid model may be generated from the mesh model 760, incorporating a thickness based upon the heart valve leaflet structure material.

Figure 8A:
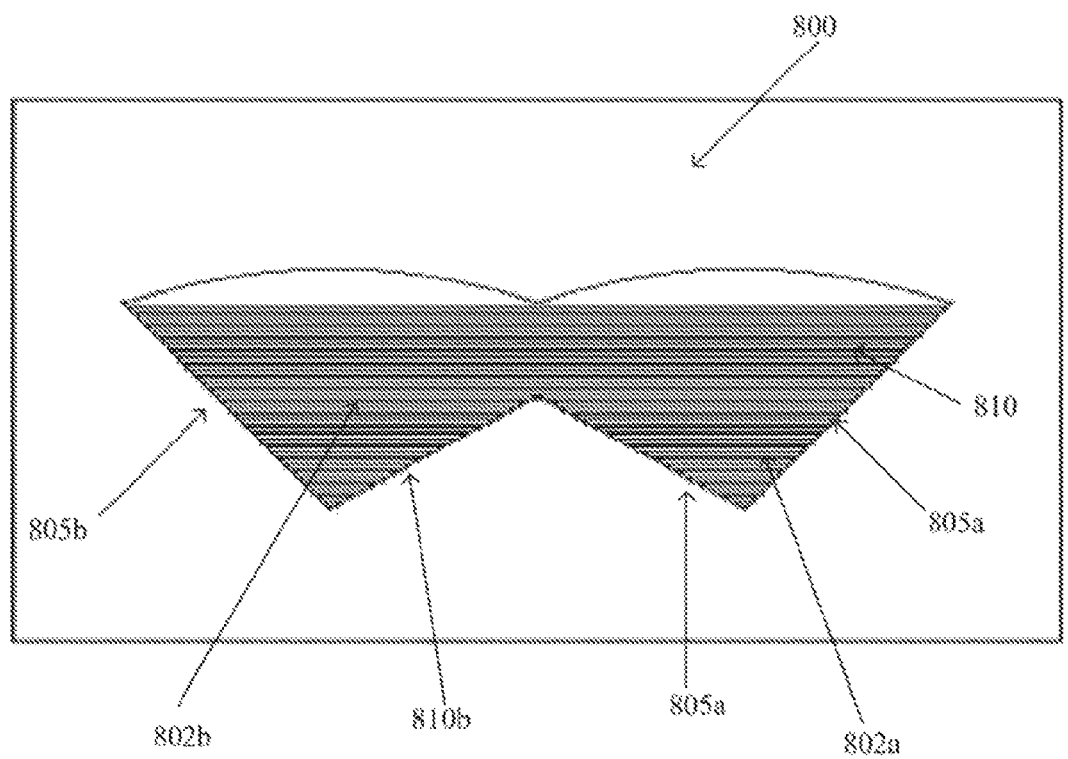
FIG. 8A illustrates an embodiment of a heart valve leaflet structure model depicting sinus structure beams in accordance with the present disclosure.
Figure 8B:
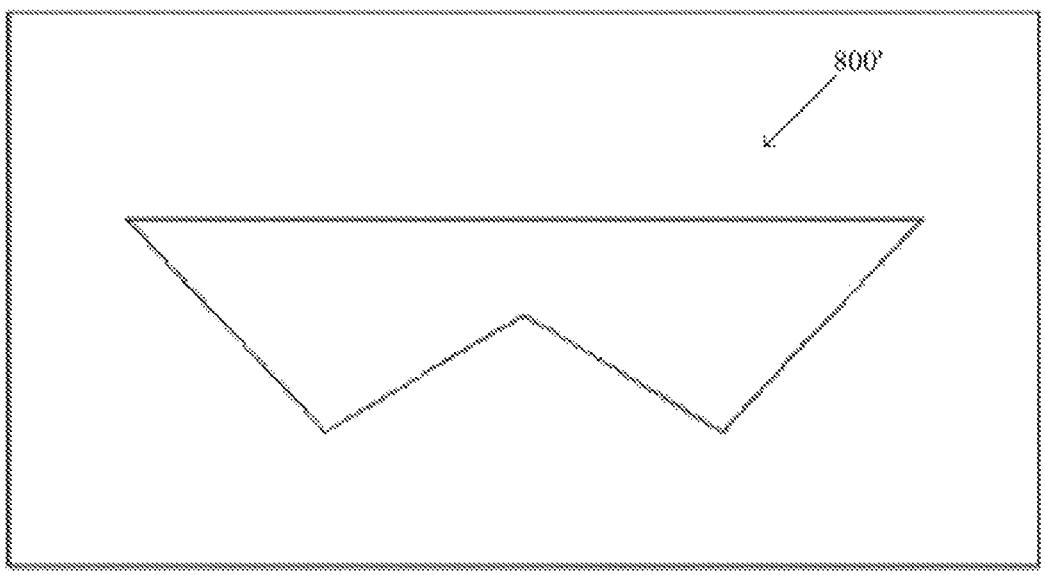
FIG. 8B illustrates an embodiment of a sinus stencil model to be used in simulations with the heart valve leaflet structure model in FIG. 8A in accordance with the present disclosure.
Figure 8C:
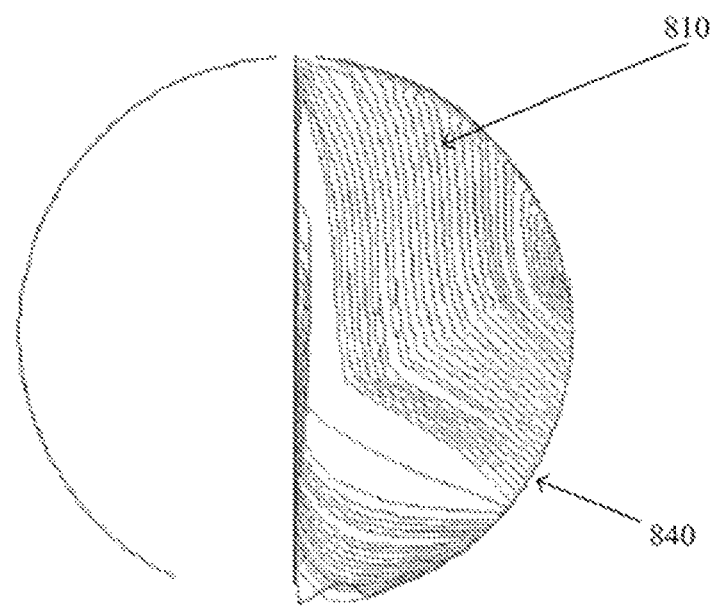
FIG. 8C illustrates an embodiment of a sinus structure model with sinus structure beams pined against the inner surface of a conduit in accordance with the present disclosure.
Figure 8D:
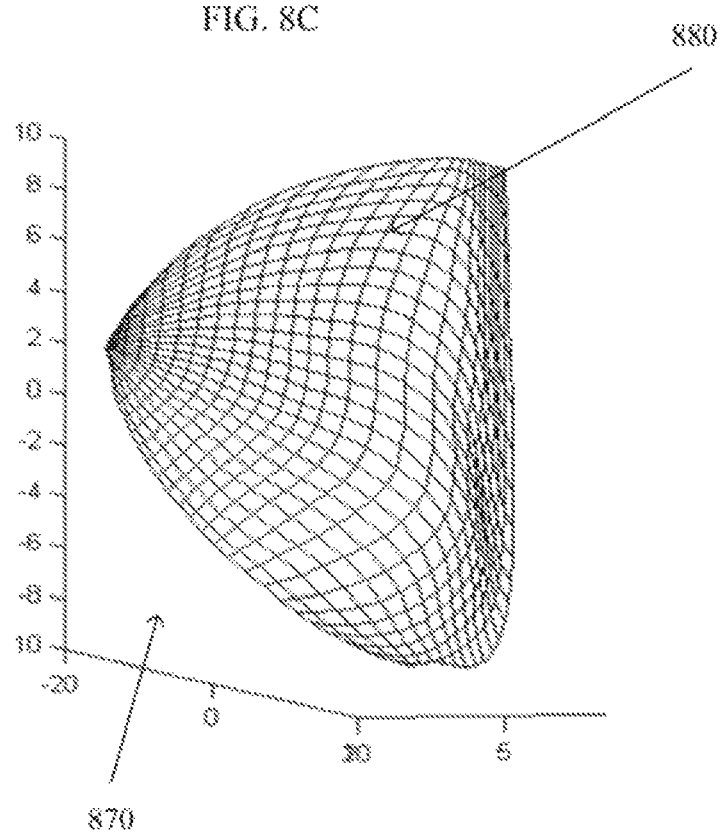
FIG. 8D illustrates an embodiment of a point-element aggregate mesh representation in accordance with the present disclosure.

FIGS. 8A and 8B illustrate non-limiting examples of results that may be obtained from an embodiment of a leaflet structure modeling computation as disclosed above. FIG. 8A illustrates a model 800 of a heart valve leaflet structure having a pair of leaflets. Sinus edges 805a,b and 810a,b are illustrated. Two sinus structures, 802a and 802b are illustrated having sinus structure beams (such as 810) dividing the sinus structures. FIG. 8B illustrates a sinus stencil 800' that may be used for mapping the heart valve leaflet structure 800 onto the inner surface of a conduit. FIG. 8C illustrates an embodiment of a non-limiting example of a result of mapping sinus edges 805*a,b* and 810*a,b* onto the inner surface of a conduit model 840. It may be appreciated that sinus structure beams 810 may form a complex two dimensional structure. FIG. 8D illustrates a non-limiting example of a point-element aggregate mesh representation 870 that may result from heart valve leaflet structure modeling. Intersections 880 of the mesh may represent the locations of member point of a point-element aggregate.

After a solid model of the leaflets has been generated, a performance of the heart valve leaflet structure model may be assessed according to one or more fluid flow analytical calculations. In some non-limiting embodiments, fluid flow analytical methods may include CFD and FSI analyses. Fluid flow analytical methods may be used to assess the performance of the heart valve leaflet structure model. Fluid flow parameters that may be entered as part of the fluid flow analytical methods may include, without limitation, one or more of cardiac and vascular geometry, patient blood flow parameters, size and/or weight of the patient, size/curvature of the conduit, a cardiac output of a patient's heart, and patient blood pressure. In one non-limiting example, fluid flow parameters associated with a patient may be acquired by direct quantitative and qualitative measurement of the patient. In another non-limiting example, average values or reference values of such fluid flow parameters may be acquired from clinical literature or other computational simulations. Fluid flow parameters may then be used in the one or more fluid flow calculations to provide a three-dimensional blood flow and pressure field along the RVOT of the patient. Flow fields may be produced to simulate diastole, systole, or any intermediate period within the cardiac cycle. Flow field and pressure information, along with parameters associated with the patient's RVOT, may be supplied to a solid structural modeling simulation that may predict the shape of the heart valve leaflet structure during multiple points in the cardiac cycle.

After each heart valve leaflet structure model has been analyzed, a value of a valve performance cost function may be determined based on an performance of the heart valve leaflet structure model according to the one or more optimization analyses. A heart valve leaflet structure optimization method may then include providing iterative incremental changes to one or more of leaflet modeling parameters and re-modeling the heart valve leaflet structures. An optimal set of leaflet modeling parameters may thus be found that may minimize a valve performance cost function. In one non-limiting embodiment, a valve performance cost function may be based upon the effective orifice area of the heart valve leaflet structure during systole and regurgitant flow during diastole. In another non-limiting embodiment, a valve performance cost function may be based on a ratio of the conduit area closed to fluid flow to the area open to fluid flow. In another non-limiting embodiment, a valve performance cost function may be based on a rate of valve opening or closing. In yet another non-limiting embodiment, a valve performance cost function may be based on a ratio of regurgitant flow rate during diastole to the forward flow rate during systole.

At the completion of the optimization calculation, a set of heart valve leaflet size parameters may be calculated. In one non-limiting embodiment, a set of heart valve leaflet size parameters may be supplied to a user by a computing device. Thus, with reference to a two-leaflet valve leaflet structure as illustrated in FIG. 3D, computing device calculations may provide values for outer lengths (305*a* and 305*b*), inner lengths (310*a* and 310*b*), heights (320*a* and 320*b*), widths (335*a* and 305*b*), fan structures (315*a* and 315*b*), fan structure heights (340*a* and 340*b*), and commissure length (330). A user of the modeling and optimization calculations may then use one or more of these computing device-calculated heart valve leaflet size parameters for fabricating one or more heart valve leaflet structures. For example, a user may use the calculated values for outer lengths, inner lengths, heights, widths, fan structures, fan structure heights, and commissure length. In an alternative embodiment, a computing device may also provide a heart valve leaflet structure stencil based at least in part upon these calculated heart valve leaflet size parameters. A heart valve leaflet structure stencil may be produced by an output device, such as a printer, for use by a user. A user may then take the heart valve leaflet structure stencil and apply it to a thin sheet of material for making the heart valve leaflet structure, and cut out the heart valve leaflet structure based on the heart valve leaflet structure stencil. The shapes and/or metrics thus calculated may be used by a health care provider, a fabricator, or a manufacturing facility to produce a variety of heart valve structures including, but not limited to, single leaflet, two-leaflet, or three leaflet heart valve structures.

In addition to heart valve leaflet size parameters related to a heart valve leaflet structure, a user may also receive sinus stencil size parameters. Thus, with reference to a two-leaflet valve leaflet structure sinus stencil as illustrated in FIG. 3E, a computing device calculations may provide values for outer lengths (305*a*' and 305*b*'), inner lengths (310*a*' and 310*b*'), heights (320*a*' and 320*b*'), widths (335*a*' and 305*b*'), and commissure length (330'). In an embodiment in which a sinus stencil additionally incorporates fan structures, the sinus stencil size parameters may also include parameters to define the fan structures, including without limitation fan structure heights. A user of the modeling and optimization calculations may then use one or more of these computing device-calculated values for fabricating one or more sinus stencils that may be applied to the inner surface of a conduit for marking the placement of the heart valve leaflet structure, as disclosed above. In another embodiment, a computing device may also provide the sinus stencil based at least in part upon the calculated sinus stencil size parameters. A sinus stencil provided by a computing device may be provided to a user from a printer device associated with the computing device.

As disclosed above, in one non-limiting embodiment, an artificial heart valve structure may be composed of a conduit, a heart valve leaflet structure, and one or more conduit sinus structures. In an alternative embodiment, an artificial heart valve structure may further incorporate one or more biodegradable structures. Such a heart valve structure may be conveniently referred to as a hybrid tissue-engineered valved conduit (hybrid TEVC). A hybrid TEVC may include, in one non-limiting example, a conduit constructed of synthetic material and having a cross section forming a partially closed circle, and a biodegradable structure which may be incorporated into the conduit wall to form an enclosed tubular structure. A hybrid TEVC may also include and one or more heart valve leaflet structures, and one or more conduit sinus structures disposed within the conduit.

Figure 9:
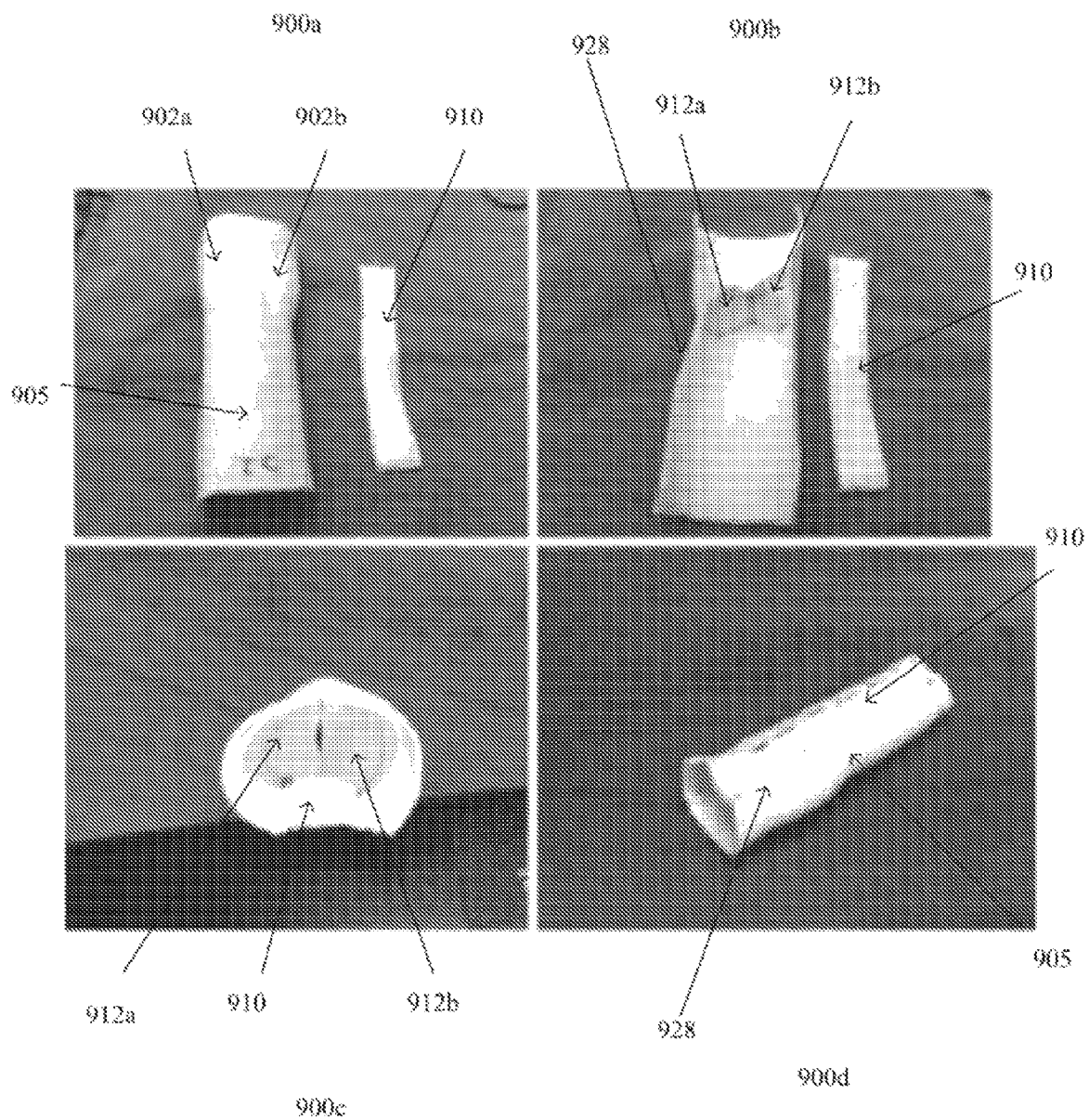
FIG. 9 illustrates embodiments of a hybrid tissue-engineered heart valve structure in accordance with the present disclosure.

FIG. 9 illustrates several views of an embodiment of a hybrid TEVC. View 900*a* illustrates a "back" view of an embodiment of a hybrid tissue-engineered valved conduit 905. The material of the conduit 905 as illustrated in view 900*a* may be a synthetic biocompatible and/or hemocompatible polymer that may include, as non-limiting examples, PTFE or ePTFE. View 900*a* also illustrates a pair of conduit sinus structures 902*a* and 902*b* that may be incorporated into a conduit 905 wall. Next to the conduit 905 may be observed a portion of a biodegradable structure 910.

View 900*b* illustrates a "front" view of the TEVC. It may be appreciated that the conduit may not be completely closed, but may have one or more conduit breaches 928 along the conduit wall. Each breach may include at least a pair of conduit breach edges from the from conduit wall. In one non-limiting embodiment, one or more conduit breaches 928 may extend along the entire long axis of a conduit. In another embodiment, a conduit breach 928 may extend only partly along the long axis of a conduit. In still another embodiment, multiple conduit breaches 928, each extending along a portion of the long axis of a conduit wall, may be dispose in a helical pattern. In one non-limiting example, such multiple conduit breaches 928, disposed in a helical pattern, may overlap along one or more circumferential portions of the conduit wall. In yet another example, such multiple conduit breaches 928, disposed in a helical pattern, may not overlap along any circumferential portions of a conduit wall. In addition, heart valve leaflets 912*a* and 912*b* may be observed in view 900*b*. A portion 910 of a biodegradable structure may be observed next to the body of a hybrid TEVC.

View 900*c* illustrates a cross-sectional view of an embodiment of a hybrid TEVC. Two heart valve leaflets 912*a* and 912*b* may be observed in view 900*c* as well. In addition, a portion of a biodegradable structure 910 may be observed as being incorporated into the conduit of the hybrid TEVC. In one non-limiting embodiment, a biodegradable structure 910 may have at least two sides, in which each side may be affixed to a conduit breach edge. View 900*d* illustrates the a biodegradable structure 910 affixed into a conduit breach 928 of the hybrid TEVC 905. Biodegradable structure 910 may be affixed to the conduit breach edges via one or more of laser beam welding, monocoque technique, heat or chemical welding, and/or the use of an adhesive.

Although FIG. 9 illustrates several views of a hybrid TEVC in which a conduit breach extends essentially along a long axis of the conduit, it may be appreciated that one or more conduit breaches may be oriented according to alternative geometries. In one non-limiting example, a conduit breach may take the form of a helical curve traversing the length of a conduit. In yet another embodiment, one or more conduit beaches may traverse essentially one or more circumferences of a conduit. In yet another embodiment, one or more conduit breaches may be disposed along a conduit wall at one or more angles with respect to the long axis of the conduit. En one non-limiting embodiment, multiple conduit breaches may form one or more continuous breach structures. In yet another non-limiting embodiment, multiple conduit breaches may be separate, and not form a continuous breach structure. In one non-limiting embodiment, a conduit breach may be composed of a single straight line segment. In another non-limiting embodiment, a conduit breach may be composed of a single curved line segment. In yet another non-limiting embodiment, a conduit breach may be composed of a serrated line segment. It may be appreciated that a conduit breach may be composed of one or more straight or curved line segments arranged in any convenient shape.

It may be further understood that one or more biodegradable structures may be incorporated into one or more conduit breaches. In one non-limiting example, as illustrated in FIG. 9, a single biodegradable structure 910 may be incorporated into the conduit wall along a single conduit beach 928. In another non-limiting example, multiple biodegradable structures may be aligned for incorporation into a single conduit breach. In still another embodiment, multiple biodegradable structures may be provided, each biodegradable structure being incorporated into the conduit wall at a separate conduit breach.

A biodegradable structure in the hybrid TEVC may be composed of one or more materials that may degrade within a body over some period of time. In one non-limiting example, one or more biodegradable structures may be made from poly(glycerol sebacate). In another non-limiting example, one or more biodegradable structures may be a composite, combining multiple synthetic materials. In another non-limiting example, one or more biodegradable structures may be made from poly(glycerol sebacate) encapsulated by a sheath of poly(caprolactone). In a non-limiting example, poly(caprolactone) may have been formed using electrospinning techniques to improve its mechanical and biological properties. In another non-limiting example, one or more biodegradable structures may include any other degradable biocompatible and/or hemocompatible material. It may be appreciated that a hybrid TEVC composed of multiple biodegradable structures may include a number of biodegradable structures having essentially the same composition. Alternatively, multiple biodegradable structures may include a number of biodegradable structures having differing compositions.

In one embodiment of a hybrid TEVC, a biodegradable structure may be replaced over time by autologous tissue, thereby allowing the heart valve structure to enlarge as the patient grows. In one non-limiting embodiment, a biodegradable structure 910 may be incorporated into a heart valve structure and implanted within a patient. In such an embodiment, cells from a patient may migrate into a biodegradable structure 910 over time to replace the material from which the biodegradable structure may be fabricated. In another non-limiting embodiment, a biodegradable structure 910 may be seeded with cells prior to implantation into a patient. Seeded cells may include, without limitation, autologous cells harvested from the patient. Examples of autologous cells may include, without limitation, one or more of CD34 cells, mesenchymal cells, myocytes, smooth muscle cells, endothelial cells, and human cardiac stem cells. In another embodiment, the biodegradable structure may include collagen fibers. In other non-limiting embodiments, a biodegradable structure may also include growth or other trophic factors, to promoted biocompatibility and/or hemocompatibility, or other biologically active materials to provide more effective therapies.

A hybrid TEVC may be fabricated from a heart valve structure as disclosed above. A heart valve structure, including one or more heart valve leaflet structures and or conduit sinus structures, may be obtained. One or more conduit breaches may be fabricated in the conduit wall, each conduit breach having a pair of conduit breach edges. The one or more conduit breaches may be formed by cutting a conduit wall including, but not limited to, slicing, cutting, or heating. Implements that may form the one or more conduit breaches may include, without limitation, scissors, a scalpel, a small knife, or a focused laser. Once one or more conduit breaches have been fabricated in a conduit wall, one or more biodegradable structures may be incorporated into the one or more conduit breaches by affixing at least a portion of the biodegradable structure to each of the conduit breach edges associated with each conduit breach. After each biodegradable structure has been affixed into a conduit wall breach, an essentially closed tubular structure composed of the conduit wall and the one or more affixed biodegradable structures may be formed. The one or more biodegradable structures may be affixed to the conduit breach edges by any appropriate means, including, without limitation, gluing, heat welding, chemical welding, and/or suturing.

EXAMPLES

Example 1

A Heart Valve Two-Leaflet Structure

A heart valve two-leaflet structure, essentially as illustrated and disclosed in FIG. 3D, was fabricated from expanded PTFE having a thickness of about 0.1 mm. A two-leaflet structure was designed for integration into a 20 mm diameter conduit. The heart valve two-leaflet structure was bilaterally symmetric about the commissure, thus measures of equivalent components between the two leaflets were about the same. The length of each inner sinus edge (equivalent to FIG. 3D 310$a,b$) was about 16 mm, the height of each leaflet (equivalent to FIG. 3D 320$a,b$) was about 15 mm, the width of each baseline (equivalent to FIG. 3D 335$a,b$) was about 27.7 mm, and each fan structure height (equivalent to FIG. 3D 340$a,b$) was about 2.8 mm. The fan structure of each leaflet was similar to the structure illustrated as 315$a,b$ in FIG. 3D, and the fan structures were bilaterally symmetric about the commissure. In addition, the commissure length (equivalent to FIG. 3D 330) was about 7 mm.

Example 2

Values for Scaling Heart Valve Leaflet Structure Parameters to a Conduit Diameter FIGS. 3D and 3E illustrate embodiments of a heart valve leaflet structure and a sinus stencil that may be used to mark the attachment of the sinus edges to a conduit as part of the method for fabricating a heart valve structure. As disclosed above, the metrics associated with the elements of the leaflets may be scaled according to the diameter of the conduit in which the heart valve leaflet structure may be inserted. Table 1, disclosed below, provides some values for the leaflet metrics, including some non-limiting ranges. The metric entry references equivalent structures in FIGS. 3D (for the leaflet) and 3E (for the stencil). Ranges are provided as examples only. The leaflet value corresponds to the metric for a heart valve leaflet, The sinus stencil value corresponds to the metric for an equivalent sinus stencil. The values in Table 1 are scaling values to conduit diameters, and may be used as multipliers to the conduit diameter to provide the appropriate length or width. Thus, a heart valve leaflet structure used in a conduit with a diameter of about 10 mm, may have a height of about 8.1 mm.

TABLE 1

| Leaflet Metric | Leaflet Value | Leaflet Range | Sinus Stencil Value | Sinus Range |
|---|---|---|---|---|
| Sinus Inner Edge length | .81 | .75-1.0 | .77 | .7-.9 |
| Height | .77 | .7-1.0 | .77 | .7-1.0 |
| Baseline width | 1.38 | 1.3-1.7 | 1.28 | 1.2-1.5 |
| Commissure length | .34 | .3-.5 | .34 | .3-.5 |
| Fan structure height | .14 | .12-.18 | — | — |

Example 3

Simulation of Blood Flow Through a Heart Valve Structure Model Conduit

Blood flowing through a modeled heart valve structure conduit was modeled as an incompressible and Newtonian fluid with constant hemodynamic properties ($\rho$=1060 kg/m^3, $\mu$=3.71 E−3 Pa·s) without a turbulence model. A cardiovascular blood flow simulator with validated $2^{nd}$-order accurate multi-grid artificial compressibility numerical solver was used to evaluate flow through the conduits. The blood flow was simulated on a high-resolution unstructured Cartesian immersed boundary grid with finite-difference numerical treatment.

Example 4

Simulation of a Heart Valve Structure

A 20 mm diameter conduit was modeled according to the same geometric parameters which were used in a clinical application (l=15.98 mm, h=15.3 mm, w=27.7 mm, c=6.9 mm, F=2.8 mm). A solid model thus generated was found to be significantly similar to the actual valve it modeled. An analysis of fluid flow through the heart valve structure thus modeled determined that regurgitation through the heart valve structure during diastole was about 8.27 mL/s. This was determined to represent about 7.84% leakage through the valve for a cardiac cycle having a 3.7 L/min flow rate, which may be normal for children.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity. It will be understood by those within the art that, in general, terms used in this disclosure, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. A valve structure comprising:
a conduit comprising an inner conduit surface; and
a multi-leaflet structure having an open state and a closed state comprising:
a first valve leaflet, comprising a first sinus structure having a first sinus edge and a first fan structure having a first fan edge, wherein at least a portion of the first sinus edge is affixed to the inner conduit surface;
a second valve leaflet, comprising a second sinus structure having a second sinus edge and a second fan structure having a second fan edge, wherein at least a portion of the second sinus edge is affixed to the inner conduit surface; and
a commissure disposed between the first valve leaflet and the second valve leaflet,
wherein at least a portion of the first fan edge, at least a portion of the second fan edge, and at least a portion of the inner conduit surface are mutually disposed to form a valve gap in the closed state of the multi-leaflet structure.

2. The valve structure of claim 1, wherein the first sinus edge comprises a plurality of first sinus edge components and the second sinus edge comprises a plurality of second sinus components.

3. The valve structure of claim 1, further comprising:
a first sinus structure height edge comprising a first inner edge component and a first outer edge component;
a second sinus structure height edge comprising a second inner edge component and a second outer edge component;
the first inner edge component, the first outer edge component, the second inner edge component, and the second outer edge component are essentially linear;
the first inner edge component and the first outer edge component intersect to form a first sinus intersection having a first height as measured from the a first leaflet baseline width; and
the second inner edge component and the second outer edge component intersect to form a second sinus intersection having a second height as measured from the a second leaflet baseline width;
a first fan height; and
a second fan height.

4. The valve structure of claim 3, wherein a ratio of the first leaflet baseline width to a diameter of the conduit is about 0.054 to about 0.17 and a ratio of the second leaflet baseline width to a diameter of the conduit is about 0.054 to about 0.17.

5. The valve structure of claim 3, wherein a ratio of a length of the commissure to the first leaflet baseline width is about 0.18 to about 0.38.

6. The valve structure of claim 1, wherein:
the first fan edge comprises a first fan edge steep portion proximate to the first sinus edge, and a first fan edge gradual portion; and
the second fan edge comprises a second fan edge steep portion proximate to the second sinus edge, and a second fan edge gradual portion.

7. The valve structure of claim 1, further comprising a first valve sinus bounded by the inner conduit surface and the first sinus structure and a second valve sinus bounded by the inner conduit surface and the second sinus structure.

8. The valve structure of claim 1, further comprising a third valve leaflet and a second commissure disposed between the second valve leaflet and the third valve leaflet, wherein the third valve leaflet comprises a third sinus structure having a third sinus edge and a third fan structure having a third fan edge and at least a portion of the third sinus edge is affixed to the inner conduit surface.

9. A method of fabricating a heart valve structure, the method comprising:
providing a flexible conduit comprising a wall, an inner surface, and an outer surface;
providing a heart valve multi-leaflet structure;
everting the flexible conduit;
affixing the heart valve multi-leaflet structure to the inner surface; and
reverting the conduit, thereby forming a multi-leaflet valve within an interior of the conduit,
wherein the heart valve multi-leaflet structure comprises a first heart valve leaflet, comprising a first sinus edge and a first fan edge, and
a second heart valve leaflet, comprising a second sinus edge and a second fan edge,
wherein the first fan edge intersects the second fan edge at an outer commissure point, and the first sinus edge intersects the second sinus edge at an inner commissure point, thereby forming a commissure extending from the outer commissure point to the inner commissure point, wherein the first fan edge intersects the first sinus edge at a first outer leaflet point, thereby forming a first baseline extending from the first outer leaflet point to the commissure, the first baseline further having a first width as measured from the first outer leaflet point to the commissure, wherein the second fan edge intersects the second sinus edge at a second outer leaflet point, thereby forming a second baseline extending from the second outer leaflet point to the commissure, the second baseline further having a second width as measured from the second outer leaflet point to the commissure, wherein the second baseline is essentially collinear with the first baseline, wherein the first sinus edge extends from and is not coextensive with the first baseline, thereby forming a first sinus structure bounded by the first sinus edge, the commissure, and the first baseline, wherein the second sinus edge extends from and is not coextensive with the second baseline, thereby forming a second sinus structure bounded by the second sinus edge, the commissure, and the second baseline, wherein the first fan edge extends from and is not coextensive with the first baseline, thereby forming a first fan structure bounded by the first fan edge, the commissure, and the first baseline, and wherein the second fan edge extends from and is not coextensive with the second baseline, thereby forming a second fan structure bounded by the second fan edge, the commissure, and the second baseline, and wherein at least a portion of the first fan edge, at least a portion of the second fan edge, and at least a portion of the inner conduit surface are mutually disposed to form a valve gap, wherein at least a portion of the first sinus structure and a portion of the inner conduit surface are nonadjacent, thereby forming a first valve sinus bounded at least in part by at least a portion of the inner conduit surface and at least a portion of the first sinus structure, and wherein at least a portion of the second sinus structure and a portion of the inner conduit surface are nonadjacent, thereby forming a second valve sinus bounded at least in part by at least a portion of the inner conduit surface and at least a portion of the second sinus structure.

10. The method of claim 9, wherein affixing the heart valve multi-leaflet structure to the inner surface comprises affixing the first sinus edge, the second sinus edge, and the commissure to the inner surface.

11. The method of claim 9, further comprising:
providing a sinus stencil; and
marking the inner surface with a shape substantially the same as the sinus stencil.

12. The method of claim 11, wherein affixing the heart valve multi-leaflet structure to the inner surface comprises affixing the first sinus edge, the second sinus edge, and the commissure along the shape marked on the inner surface.

13. A valve structure comprising:
a conduit comprising an inner conduit surface; and
a leaflet structure having an open and a closed state comprising:
a valve leaflet, comprising a sinus structure having a sinus edge and a fan structure having a fan edge,
wherein at least a portion of the sinus edge is affixed to a portion of the inner conduit surface,
wherein at least a portion of the fan edge and at least a portion of the inner conduit surface are mutually disposed to form a valve gap in the closed state of the leaflet structure.

* * * * *